United States Patent
Eino

[19]

[11] Patent Number: 6,120,435
[45] Date of Patent: Sep. 19, 2000

[54] ENDOSCOPE SYSTEM IN WHICH OPERATION SWITCH SETS DESIGNED TO FUNCTION AND BE HANDLED SAME WAY ARE INCLUDED IN ENDOSCOPE AND IMAGE PROCESSING APPARATUS RESPECTIVELY

[75] Inventor: Teruo Eino, Hachioji, Japan

[73] Assignee: Olympus Optical Co., Ltd., Japan

[21] Appl. No.: 09/085,821

[22] Filed: May 28, 1998

[30]  Foreign Application Priority Data

Jul. 16, 1997 [JP] Japan ................................ 9-191556

[51] Int. Cl.[7] .............................................. A61B 1/045
[52] U.S. Cl. ............................................ 600/118; 348/65
[58] Field of Search ................................. 600/109, 118, 600/152, 167; 348/65, 74, 76

[56]  References Cited

U.S. PATENT DOCUMENTS

| | | | |
|---|---|---|---|
| 4,651,201 | 3/1987 | Schoolman | 600/109 |
| 4,846,155 | 7/1989 | Kimura | 600/109 |
| 4,885,634 | 12/1989 | Yabe | 600/109 |
| 4,901,143 | 2/1990 | Uehara | 600/109 |
| 4,998,972 | 3/1991 | Chin | 600/109 |
| 5,060,632 | 10/1991 | Hibino | 600/109 |
| 5,202,758 | 4/1993 | Tamburrino | 600/109 |
| 5,347,994 | 9/1994 | Takahashi | 600/109 |
| 5,441,043 | 8/1995 | Wood | 600/109 |
| 5,469,840 | 11/1995 | Tanii | 600/109 |
| 5,583,566 | 12/1996 | Kanno | 600/109 |
| 5,646,680 | 7/1997 | Yajima | 600/109 |
| 5,697,885 | 12/1997 | Konomura | 600/109 |
| 5,871,439 | 2/1999 | Takahashi | 600/118 |

Primary Examiner—John P. Leubecker
Attorney, Agent, or Firm—Ostrolenk, Faber, Gerb & Soffen, LLP

[57]  ABSTRACT

Operation button sets that are actuated with the same operation switches are included in an endoscope in which an imaging device is incorporated and in an image processing apparatus for processing an image taken by the imaging device. The operation buttons are connected to a CPU in the image processing apparatus. Using whichever one of the operation button sets a user chooses to operate the endoscope system, the user can execute functions such as displaying a still image or enlarging and displaying an image by following the same handling procedure for each operation button set. Thus, the user is relieved from learning a plurality of handling procedures.

26 Claims, 15 Drawing Sheets

| IMAGE NUMBER | DATE OF COLLECTION AND RECORDING | TIME OF COLLECTION AND RECORDING |
|---|---|---|
| 1 | 97. 1. 10 | 13:00 |
| 2 | 97. 1. 10 | 13:10 |
| 3 | 97. 1. 12 | 10:05 |
| ⋮ | ⋮ | ⋮ |

| | BUTTON (SWITCH) | | | | | | | ENCORDED OUTPUT | | |
|---|---|---|---|---|---|---|---|---|---|---|
| | S1 | S2 | S3 | S4 | S5 | S6 | S7 | Q2 | Q1 | Q0 |
| STATE | ON | — | — | — | — | — | — | 1 | 1 | 1 |
| | OFF | ON | — | — | — | — | — | 1 | 1 | 0 |
| | OFF | OFF | ON | — | — | — | — | 1 | 0 | 1 |
| | OFF | OFF | OFF | ON | — | — | — | 1 | 0 | 0 |
| | OFF | OFF | OFF | OFF | ON | — | — | 0 | 1 | 1 |
| | OFF | OFF | OFF | OFF | OFF | ON | — | 0 | 1 | 0 |
| | OFF | OFF | OFF | OFF | OFF | OFF | ON | 0 | 0 | 1 |
| | OFF | OFF | OFF | OFF | OFF | OFF | OFF | 0 | 0 | 0 |

— INDICATES THAT WHICHEVER SWITCH IS ON OR OFF DOES NOT AFFECT OUTPUT

ENDOSCOPE SYSTEM IN WHICH OPERATION SWITCH SETS DESIGNED TO FUNCTION AND BE HANDLED SAME WAY ARE INCLUDED IN ENDOSCOPE AND IMAGE PROCESSING APPARATUS RESPECTIVELY

BACKGROUND OF THE INVENTION

1. Field of the Invention

The present invention relates to an endoscope system in which operation switches such as a freeze switch used to instruct display of a still image are designed to function and be handled in the same way are included in an endoscope and image processing apparatus respectively.

2. Description of the Related Art

Endoscopes have been widely adopted in the field of medicine and the fields of industries. FIG. 1 shows an endoscope system 121 known in the prior art. The endoscope system 121 comprises an electronic endoscope 122, a light source apparatus 123 for supplying illumination light to a light guide in the electronic endoscope 122, an image processing apparatus 124 for processing an image signal taken by an imaging means, which is not shown, included in the electronic endoscope 122, and a monitor 125 for displaying a standard video signal processed by and output from the image processing apparatus 124.

The image processing apparatus 124 may be provided with several additional functions, such as the ability to vary the brightness and tone of an image and to freeze an image. These functions are controlled by handling switches 126 formed on the image processing apparatus 124.

FIG. 2 shows another endoscope system 121' that has become popular in recent times. In the endoscope system 121', like the endoscope system 121 shown in FIG. 1, functions installed in the image processing apparatus 124 can be controlled using switches 126 formed on the image processing apparatus 124. The more frequently-used functions, for example, functions of freezing an image and of varying the brightness of an image, can be operated using buttons 127 formed on an operation unit of an electronic endoscope 122.

The switches 126 formed on the image processing apparatus 124 and the buttons 127 formed on the operation unit of the electronic endoscope 121 differ in number and layout, and are therefore different in their respective manner of handling. Users must therefore peruse operation manuals so as to familiarize themselves with the ways of handling them.

SUMMARY OF THE INVENTION

Accordingly, an object of the present invention is to provide an endoscope system enabling a user who is familiar with only one manner of operation, to select a convenient operating member from among a plurality of operating members formed on different components of the endoscope system such that any selected operating member may be handled in the same way.

An endoscope system of the present invention comprises: an endoscope including an elongated insertion unit; a light emitting means for emitting illumination light through the distal part of the insertion unit; an objective optical system located in the distal part for forming an image of an object illuminated by the illumination light; and an imaging device for photoelectrically converting the image; an image processing apparatus for processing an image signal output from the imaging device and producing a standard video signal; a monitor for displaying the standard video signal; first and second operating members connected to the endoscope and image processing apparatus, respectively, each having a corresponding operation switch set; and a control means connected to the first and second operating members for controlling any of the functions installed in the endoscope system in response to the handling of either of the first and second operating members. Using either the first or second operating members, a desired function can be executed by handling the operating members in the same way. Users can operate the endoscope system by handling any operation switch set according to the same handling procedure and need not learn a plurality of ways of handling different operation switch sets which have mutually different structures.

BRIEF DESCRIPTION OF THE DRAWINGS

FIG. 3 is a block diagram showing the configuration of an endoscope system of the first embodiment;

FIG. 4 is a block diagram showing the configuration of an image processing apparatus;

FIG. 6 is a block diagram showing the configuration of an endoscope system of the third embodiment;

FIG. 7 is a diagram showing an image and graphic buttons appearing on a monitor screen;

FIG. 8 is a diagram showing a list of image data items appearing on the monitor screen when a List graphic button is selected;

FIG. 9 is a diagram showing multiple images appearing on the monitor screen when a MULTI graphic button is selected;

FIG. 13 is block diagram showing the configuration of an of an endoscope system of the seventh embodiment.

FIG. 14 is a diagram showing an example of the internal wiring of an electronic endoscope;

FIG. 15 is a diagram showing the internal wiring of an electronic endoscope;

FIG. 16 is a diagram showing the relationship of inputs and outputs of an encoder shown in FIG. 15;

FIG. 17 is a block diagram showing the configuration of an endoscope system of the ninth embodiment;

FIG. 18 is a diagram showing how to handle operation buttons formed on an operation unit of an electronic endoscope;

FIG. 20 is a block diagram showing the configuration of an endoscope system of the eleventh embodiment; and FIG. 21 is a sectional view showing the structure of the distal part of an electronic endoscope.

DESCRIPTION OF THE PREFERRED EMBODIMENTS

Figure 1:
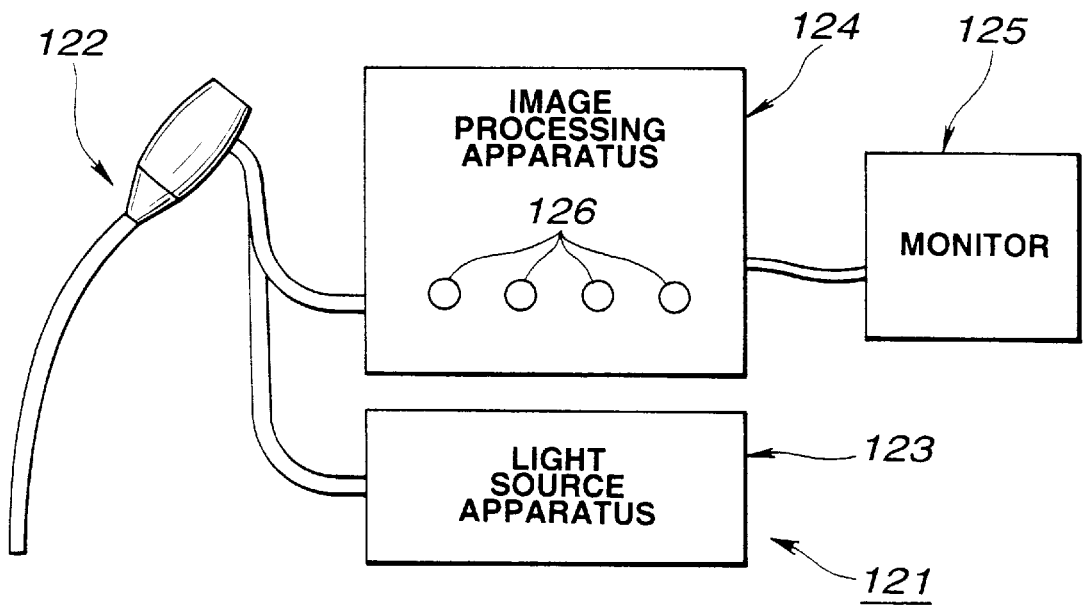
FIG. 1 is a block diagram schematically showing the configuration of a prior art endoscope system.
Figure 2:
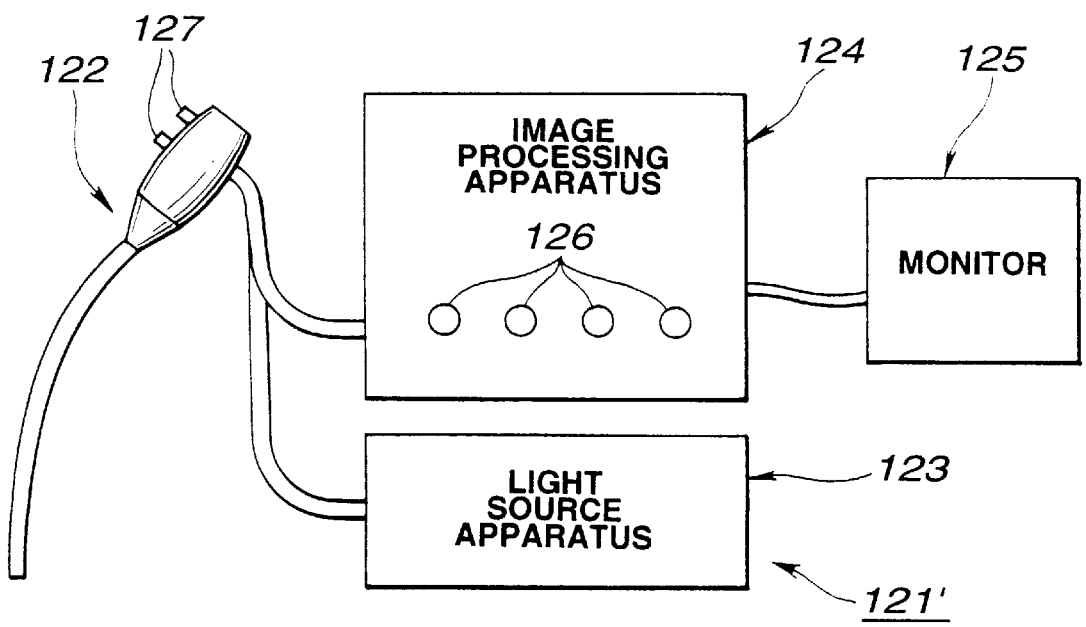
FIG. 2 is a block diagram schematically showing the configuration of another prior art endoscope system.

Referring to the drawings, embodiments of the present invention will be described.

(First Embodiment)

Figure 3:
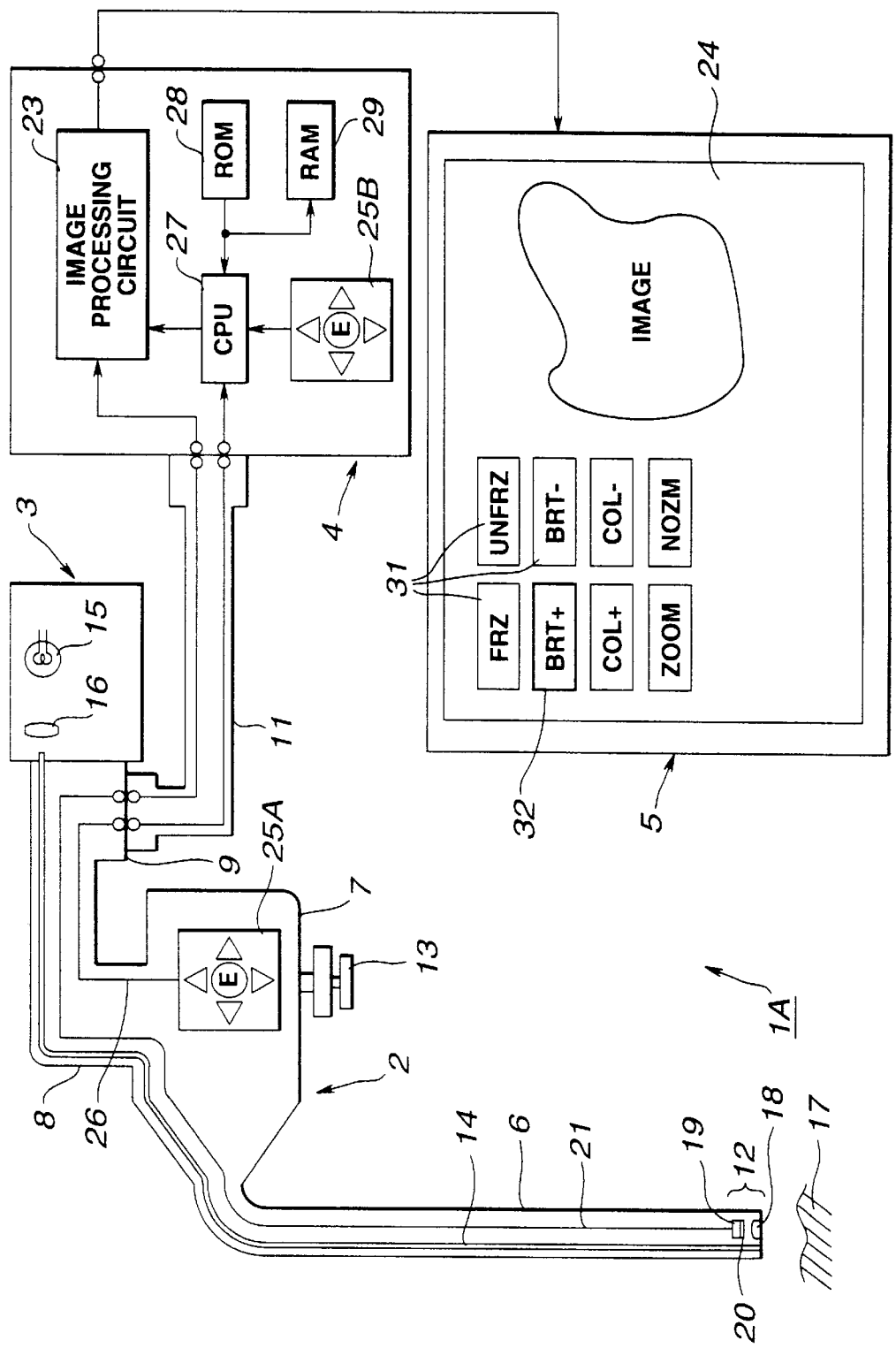
FIGS. 3 and 4 relate to the first embodiment of the present invention.

FIG. 3 shows an endoscope system 1A of the first embodiment of the present invention. In this embodiment, operating members designed to function and be operated in the same way are included in an endoscope and image processing apparatus respectively. Either of the operating members is used to move a cursor on a screen to a function mark so that a function associated with the mark can be executed.

An endoscope system 1A shown in FIG. 3 comprises an electronic endoscope 2 in which an imaging device for photoelectrical converting a signal is incorporated, a light source apparatus 3 for supplying illumination light to the electronic endoscope 2, an image processing apparatus (or signal processing apparatus) 4 for driving the imaging device and processing an output signal of the imaging device, and a monitor 5 for displaying a standard video signal output from the image processing apparatus 4.

The electronic endoscope 2 includes an insertion unit 6 that is elongated and flexible, an operation unit 7 (hand-held unit) formed at the back end of the insertion unit 6 and grabbed by a user for operation, and a universal cord 8 extending from the operation unit 7. A connector 9 freely attachable or detachable to or from the light source apparatus 3 is attached to the end of the universal cord 8. An electric connector spliced with one end of a signal cable 11 is joined with the connector 9. An electric connector spliced with the other end of the signal cable 11 is freely attachable or detachable to or from the image processing apparatus 4.

Moreover, the insertion unit 6 comprises a distal part 12 formed at the tip of the insertion unit, a bending part formed at the back end of the distal part and capable of bending freely, and a flexible part extending from the back end of the bending part to the front end of the operation unit 7 and having flexibility. The bending part can be angled in a desired direction by handling a bending knob 13 located on the operation unit 7.

A light guide 14 for propagating illumination light is provided along the interior of the electronic endoscope 2. When the connector 9 is linked to the light source apparatus 3, illumination light emanating from a lamp 15 in the light source apparatus 3 is supplied to one end surface of the light guide, which is an incidence surface thereof, via a condenser 16.

The illumination light propagated along the light guide 14 is emitted through the other end surface of the light guide fixed to an illumination window of the distal part 12, and illuminates an object 17 such as a lesion or the like.

Light reflected from the illuminated object 17 forms an image on a solid-state imaging device, for example, a charge-coupled device (hereinafter CCD) 19 located at the position of the image plane of an objective lens 18 fitted in an observation window adjoining the illumination window by means of the objective lens 18. An imaging surface of the CCD 19 is provided with a mosaic filter 20 for optically separating colors. After being separated into color components by a color filter array forming the mosaic filter 20, incident light forms an image on the imaging surface of the CCD 19.

An image signal or imaging signal photoelectrically converted by the CCD 19 is input to an image processing circuit 23 in the image processing apparatus 4 over a signal line 21 in the electronic endoscope 2 and a signal line contained in the signal cable 11.

The image processing circuit 23 converts the image signal into a standard video signal, and displays an object image taken by the CCD 19 as an endoscopic image in, for example, a right-handed endoscopic image display area on a display plane (or monitor screen) 24 of the monitor 5.

According to this embodiment, a first operation button set (or operation switch set) 25A and second operation button set 25B are located on the operation unit 7 of the electronic endoscope 2 and, for example, on the front panel of the image processing apparatus 4, respectively.

The sets each include five push buttons and are analogous to each other in terms of the shapes and layout of the buttons. The sets each include four direction buttons used to instruct up, down, leftward, and rightward movements, and an E button used to effect a function of entering an instruction.

The operation button set 25A is connected to a central processing unit (CPU) 27 in the image processing apparatus 4 via the signal line 26 in the electronic endoscope 2 and the corresponding signal line contained in the signal cable 11. Operation information produced by handling the operation button set 25A is transmitted to the CPU 27 serving as a control means.

Moreover, the operation button set 25B is also connected to the CPU 27. Operation information produced by handling the operation button set 25B is transmitted to the CPU 27.

The CPU 27 is connected to a ROM 28 in which software (specifically, programs and relevant data items) is stored and to a RAM 29 which is used as a work area for executing software or used to temporarily store data.

Figure 4:
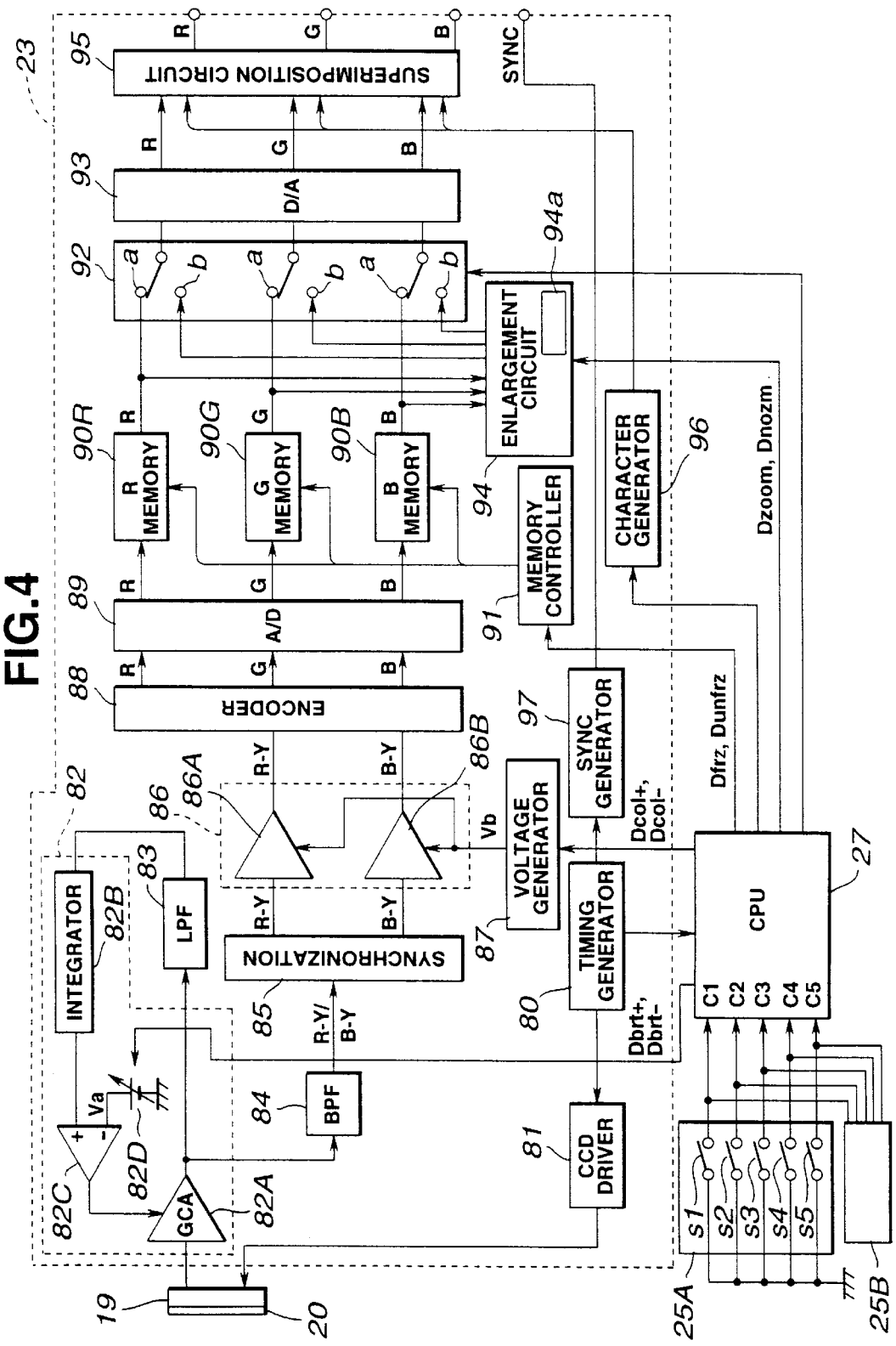

FIG. 4 shows the configuration of the image processing circuit 23.

The image processing circuit 23 includes a CCD driver 81. The CCD driver 81 produces a CCD driving signal, applies the signal to the CCD 19, and outputs a signal photoelectrically converted by the CCD 19. A given timing signal is input from the timing generator 80 to the CCD driver 81. Synchronously with the timing signal, the CCD driving signal is output.

A signal output from the CCD 19 is input to a gain control amplifier 82A used to form an AGC circuit 82. After being amplified, the signal is input to a low-pass filter 83 and bandpass filter 84. Consequently, a luminance signal Y and color-difference signals R-Y and B-Y for line sequential imaging are produced.

The luminance signal Y is input to an integrator 82B, an integrated in units of a given period, for example, one to several frames. Consequently, a signal indicating an average level of brightness for the given period is applied to one input terminal of a differential amplifier 82C. A reference voltage Va used to determine a reference brightness level and supplied from a reference power supply 82D is applied to the other input terminal of the differential amplifier 82C.

The differential amplifier 82C applies an error signal indicating an error from the reference voltage Va to a gain control terminal of the gain control amplifier 82A. Thus, a luminance level indicated by an image signal output from the gain control amplifier 82A is retained at the reference brightness level determined by the reference voltage Va.

In this embodiment, the reference power supply 82D is realized with a variable voltage circuit and is designed to raise or lower the reference voltage Va in response to a brightness increase instruction signal Dbrt+ or brightness decrease instruction signal Dbrt- Sent from the CPU 27. When the reference voltage Va is raised, a gain permitted by the gain control amplifier 82A gets larger and the signal level of an image signal gets higher. On the other hand, when the reference voltage Va is lowered, the gain permitted by the gain control amplifier 82A gets smaller.

The color-difference signals R-Y and B-Y for line sequential imaging are passed through a synchronization circuit 85 composed of a delay circuit and selection switch, which are not shown, to be converted into synchronized color-difference signals R-Y and B-Y, and then input to gain control amplifiers 86A and 86B constituting a color enhancement circuit 86.

A voltage Vb supplied from a voltage generator 87 is applied to the gain control terminals of the gain control amplifiers 86A and 86B. A color increase instruction signal Dcol+ or color decrease instruction signal Dcol- sent from the CPU 27 is applied to the voltage control terminal of the voltage generator 87.

When the color increase instruction signal Dcol+ is applied, the voltage Vb is raised to increase the gains permitted by the gain control amplifiers 86A and 86B. The signal levels of the color-difference signals R-Y and B-Y are then raised to increase the depths (saturations) of the colors.

When the color decrease instruction signal Dcol- is applied, the voltage Vb is lowered to decrease the gains permitted by the gain control amplifiers 86A and 86B. The signal levels of the color-difference signals R-Y and B-Y are then lowered to decrease the depths (saturations) of the colors.

The color-difference signals R-Y and B-Y output from the color enhancement circuit 86 are input to an encoder 88 for converting the color-difference signals into color signals, thus converted into color signals R, G, and B, and then input to an A/D converter unit 89.

Color signals R, G. and B digitized by the A/D converter unit 89 are written temporarily in an R memory 90R, G memory 90G, and B memory 90B, respectively. Digital color signals R, G, and B written in the memories 90R, 90G, and 90B during a previous frame are read concurrently, and output to a D/A converter unit 93 via a switch 92.

Writing or reading signals in or from the memories 90R, 90G, and 90B is controlled by a memory controller 91.

A freeze instruction signal Dfrz instructing freeze, or an unfreeze signal Dunfrz, which is sent from the CPU 27, is input to the memory controller 91. When the freeze signal Dfrz is input, the memory controller 91 inhibits writing of signals in the memories 90R, 90G, and 90B and repeatedly outputs color signals written immediately before writing inhibition so that a still image can be displayed on the monitor 24.

Moreover, when the unfreeze signal Dunfrz is input, the memory controller 91 releases inhibition of writing of signals in the memories 90R, 90G, and 90B so that a motion picture can be displayed on the monitor 24.

Digital color signals R, G, and B read from the memories 90R, 90G, and 90B are input to an enlargement circuit 94 for carrying out enlargement. An enlarged image is temporarily stored in an internal memory 94a.

An enlargement instruction signal Dzoom and enlargement release signal Dnozm sent from the CPU 27 are input to the enlargement circuit 94. When the enlargement instruction signal Dzoom is input, enlargement is carried out, and an image temporarily stored in the memory 94a is output to a switch unit 92. In this case, the CPU 27 sends a control signal so that a contact b in the switch unit 92 will be turned on and enlarged color signals will be output to the D/A converter unit 93.

The D/A converter unit 93 converts the color signals into an analog form, and outputs analog color signals R, G, and B to a superimposition circuit 95. A character signal sent from a character generator 96 is input to the superimposition circuit 95. The superimposition circuit 95 superimposes the character signal on the analog color signals R, G, and B. and outputs the resultant signals. The character generator 96 outputs a character signal as instructed by the CPU 27. The color signals R, G, and B output from the superimposition circuit 95 are output together with a synchronizing (hereinafter sync) signal SYNC sent from a sync signal generator 97 to the monitor 24. The sync signal generator 97 produces the sync signal SNYNC synchronously with a timing signal sent from the timing generator 80.

The timing signal is also input to the CPU 27. The CPU 27 carries out a control operation synchronously with the timing signal.

Ports C1 to C5 of the CPU 27 are connected to switches s1 to s5 associated with arbitrary buttons constituting the operation buttons set 25A and 25B. In FIG. 4, the switches s1 to s5 are associated with, for example, the Up, Down, Left, Right, and E buttons respectively.

When, for example, the Up button is pressed to change the off state of the switch s1 to the on state, the level at the port C1 of the CPU 27 connected to the switch s1 makes a high-to-low transition. The CPU 27 then becomes aware of the fact that the switch s1 has been activated.

The CPU 27 then operates according to a program stored in the ROM 28. When any button of the operation button set 25A or 25B is pressed, the CPU 27 executes the associated processing. Moreover, according to the stored program, the CPU 27 allows the image processing circuit 23 to display a plurality of function marks 31 in an area adjoining the endoscopic image display area on the monitor screen 24.

For example, the CPU 27 sends a character code corresponding to a function mark 31 stored in the ROM 28 to the character generator 96 in the image processing circuit 23, and allows the superimposition circuit 95 to superimpose character data of the function mark 31 on the color signals R, G, and B, which constitute a video signal and are output from the image processing circuit 24, according to a given timing. Thus, the plurality of function marks 31 are displayed on the monitor screen 24 as shown in FIG. 3.

Moreover, the CPU 27 carries out the processing of displaying one square cursor 32 on the monitor screen 24. Referring to FIG. 3, the cursor 32 is displayed on a BRT+ function mark 31. When an arrow button of the operation button set 25A or 25B is pressed, the cursor 32 is moved to a function mark 31 located in the direction of the arrow. When the E button is pressed, the image processing circuit 23 is controlled so that processing corresponding to the function associated with the function mark 31 designated by the cursor 32 will be carried out.

Specifically, when the operation button set 25A or 25B serving as an operating means is handled, an instruction signal associated with the handling operation is judged by the CPU 27. The CPU 27 sends an associated control signal to the image processing circuit 23 so as to control the image processing circuit 23, whereby a function associated with the handling operation is realized. The image processing circuit 23 thus serves as an image processing means providing the functions associated with the function marks 31.

For example, when a direction button of the operation button set (25A or 25B) is pressed, the cursor 32 can be moved to a desired function mark 31. After the cursor 32 is moved to the desired function mark 31 and the E button is pressed, the CPU 27 becomes aware of the selection and executes the selected function.

In this case, if a selected function mark is a FRZ (freeze) function mark, the CPU 27 inhibits the image processing circuit 23 from writing image signals in the R, G, and B memories 90R, 90G, and 90B, and thus sends a control signal so that an image produced immediately before the inhibition can be read repeatedly. Consequently, a still image appears on the monitor screen 24.

If a selected function mark is an UNFRZ (unfreeze) function mark, a control signal is sent in order to release inhibition of writing of image signals in the R, G, and B memories 90R, 90G, and 90B. Consequently, the still image is returned to a normal motion picture.

If a selected function mark is a BRT+ (brightness+) function mark, the CPU 27 modifies the conditions for image processing so as to increase the brightness of a displayed image. Specifically, the CPU 27 sends a control signal so as to increase a gain permitted by the gain control amplifier 82A. Consequently, the brightness of the image increases.

If a selected function mark is BRT (brightness−) function mark, the conditions for image processing are modified for decreasing the brightness of the displayed image.

If a selected function mark is a COL+ (color+) function mark, the conditions for image processing are modified for deepening the colors of a displayed image. For example, a color enhancement level set in the color enhancement circuit 86 is raised for deepening the colors of the image.

If a selected function mark is a COL− (color−) function mark, the conditions for image processing are modified for lightening the colors of a displayed image.

If a selected function mark is a ZOOM (zoom) function mark, the displayed image is zoomed. For example, the enlargement circuit 94 in the image processing circuit 23 is actuated to enlarge an image. Thus, an image displayed on the monitor screen 24 is enlarged.

If a selected function mark is a NOZM function mark, zoom is released for returning the zoomed image to a normal image.

This embodiment has advantages as described below.

Since the operation button set 25A and operation button set 25B can be handled in the same way, a user can execute a desired function by handling whichever operation button set he/she can handle more conveniently in a given use environment. Moreover, the user need only learn one manner of operation.

This obviates the occurrence of an event in which a user becomes confused due to unfamiliarity with different protocols for handling different operating means. Easy and proper handling can be achieved, and maneuverability can be improved.

Moreover, since the cursor 32 is moved to a desired function mark 31 in order to execute a function associated with the function mark, numerous functions can be provided irrespective of the number of operation buttons constituting the operation button set. Any of the numerous functions can therefore be selected and executed.

(Second Embodiment)

Next, the second embodiment of the present invention will be described with reference to FIG. 5. In this embodiment, a cursor on the screen is moved by handling the operating means. Thus, the cursor can be moved as if it were moved by handling a mouse.

Figure 5:
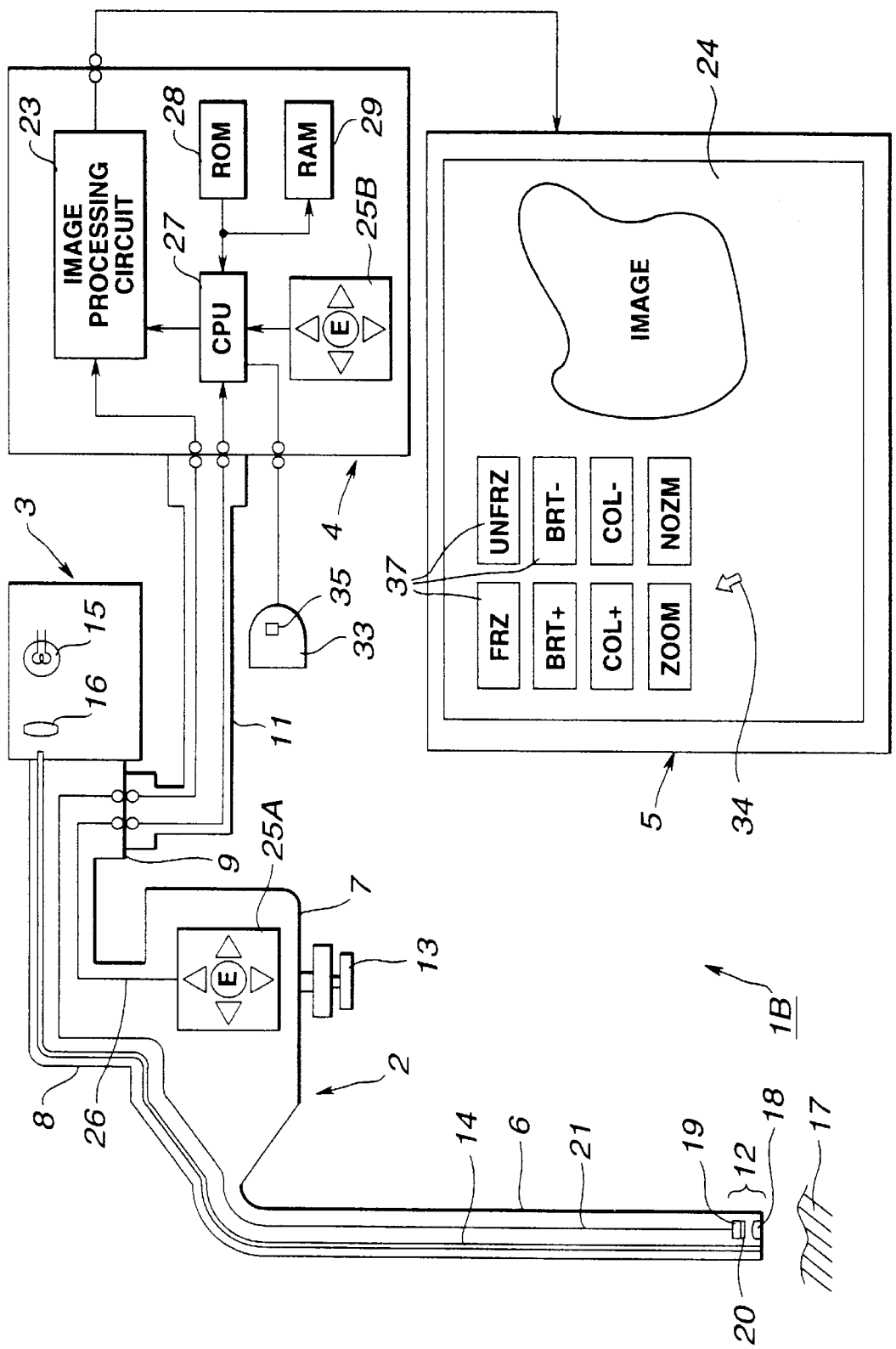
FIG. 5 is a block diagram showing the configuration of an endoscope system of the second embodiment of the present invention.

An endoscope system 1B of the second embodiment shown in FIG. 5 has, in addition to the same components as those of the endoscope system 1A shown in FIG. 3, a mouse 33. The mouse 33 is connected to the image processing apparatus 4. More particularly, the mouse 33 is connected to the CPU 27 in the image processing apparatus 4.

Graphic buttons 37 are provided as entries of functions installed in the image processing apparatus 4. The graphic buttons 37 are substantially identical to the function marks 31 in the first embodiment. The CPU 27 sends data necessary to display a cursor 34 to the image processing circuit 23. The image processing circuit 23 in turn displays the cursor 34 on the monitor screen 24 via an internal character generator 96 (see FIG. 4).

The cursor 34 displayed on the monitor screen 24 is moved to a graphic button 37 by moving the mouse 33, and a desired function is executed by clicking a mouse button 35 on the mouse 33.

The selected process performed by the image processing apparatus is executed by the CPU 27 according to software stored in the ROM 28.

Regardless of which operation button set 25A or 25B is handled, the CPU 27 executes the selected process according to the software. Assuming that a direction button of the operation button set 25A or 25B is pressed, while the button is held down, the cursor 34 moves up, down, leftward, or rightward at a constant speed. A user can thus move the cursor to a desired graphic button 37.

Thereafter, when the E button of the operation button set 25A or 25B is pressed, a desired function can be executed. In other words, pressing a direction button corresponds to moving of the mouse 33 in the direction, and the E button corresponds to the mouse button 35. When a desk or similar surface is unavailable, a user can operate the endoscope system by handling the operation button set 25A or 25B. When the desk or the like is available, the endoscope system can be operated using the mouse 33.

This embodiment has an advantage as described below.

Since the way of handling the operation button set 25A and 25B is substantially identical to the manner of handling a mouse, a user can choose an operating member he/she can handle most conveniently in a given use environment to operate the endoscope system properly. Whichever operating member is used, the monitor screen 24 is the same. The user need only learn one manner of operation.

(Third Embodiment)

Next, the third embodiment of the present invention will be described with reference to FIGS. 6 to 9. For the sake of brevity, the light source apparatus 3 and other features discussed above are omitted from FIG. 6 (the same approach is applied to the discussion of FIG. 10 and other figures to be referenced later).

In this embodiment, the three apparatuses of the endoscope, image processing apparatus, and image collection and recording apparatus have an operating member designed to function and be handled in the same way. Operation information produced by handling each operating member is treated comprehensively by the image collection and recording apparatus. If the operation information indicates a request for a function of the image processing apparatus, the request is transmitted from the image collection and recording apparatus to the image processing apparatus. The image processing apparatus then carries out the corresponding processing.

Figure 6:
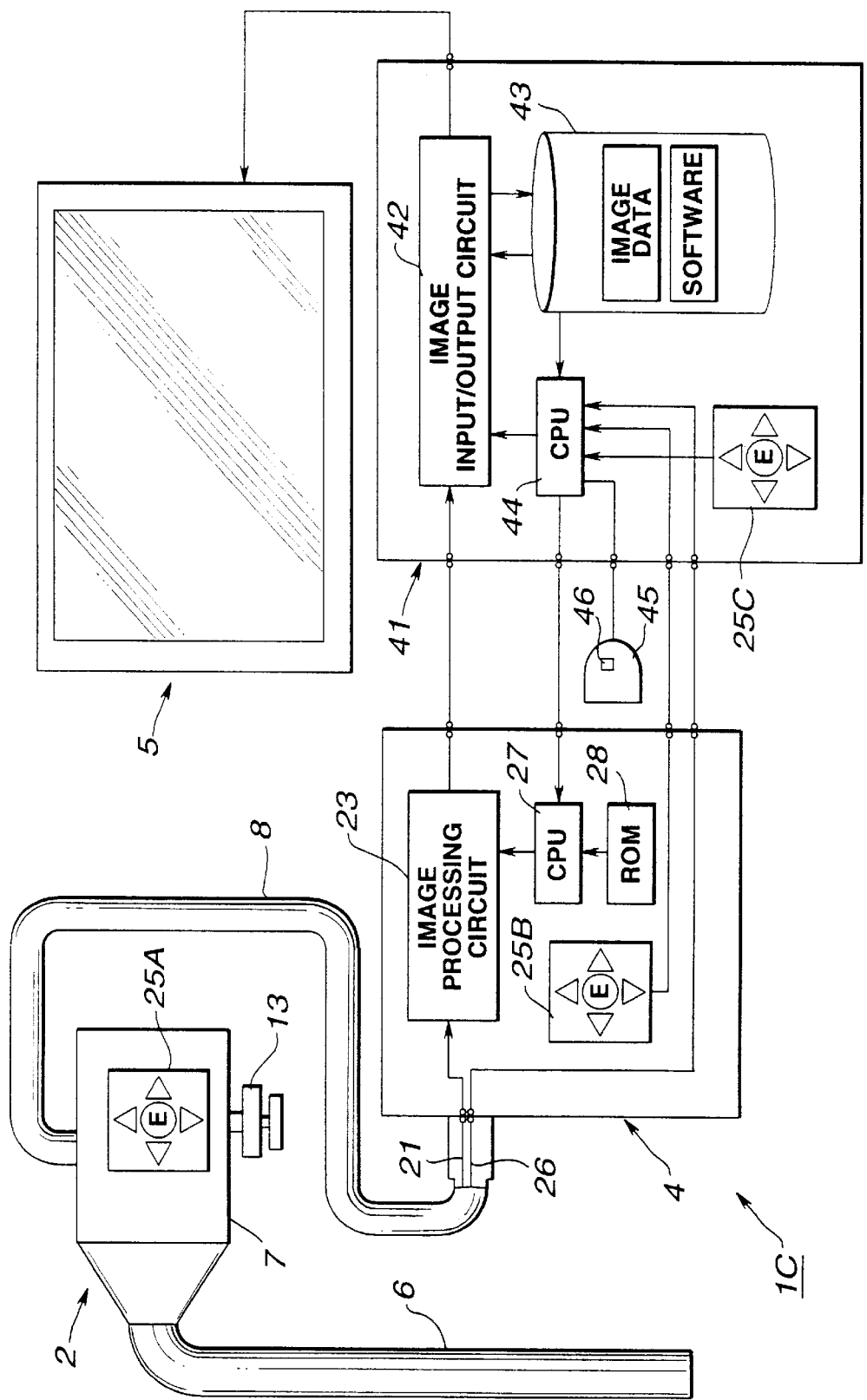
FIGS. 6 to 9 relate to the third embodiment of the present invention.

An endoscope system 1C of the third embodiment shown in FIG. 6 has, in addition to the same components as those of the endoscope system 1A shown in FIG. 3, an image collection and recording apparatus 41 for recording or reproducing image data represented by a video signal output from the image processing apparatus 4. The image collection and recording apparatus 41 is interposed between the image processing apparatus 4 and monitor 5.

The image collection and recording apparatus 41 includes an image input/output circuit 42 for outputting a standard video signal input from the image processing circuit 23 to the monitor 5 or for recording the video signal in a recording means, and further includes a hard disk 43 serving as the recording means in which image data or the like is recorded, an operation button set 25C having the same structure as the operation button set 25A included in the electronic endoscope 2, and a CPU 44 for comprehensively treating operation information produced by handling the operating members. A mouse 45 having a mouse button 46 is connected to the CPU 44.

An image signal produced by the electronic endoscope 2 is processed by the image processing circuit 23 in the image processing apparatus 4, thus becoming a standard video signal. The standard video signal is input to the image collection and recording apparatus 4.

Under the control of the CPU 44, the image input/output circuit 42 in the image collection and recording apparatus 41 (a) sends an input video signal to the monitor 5 so that the video signal can be displayed, (b) records the video signal as image data in the hard disk 43, and (c) reads image data recorded in the hard disk 43, restores the image data to a video signal, and sends the video signal to the monitor 5 for display.

Figures 7, 8:
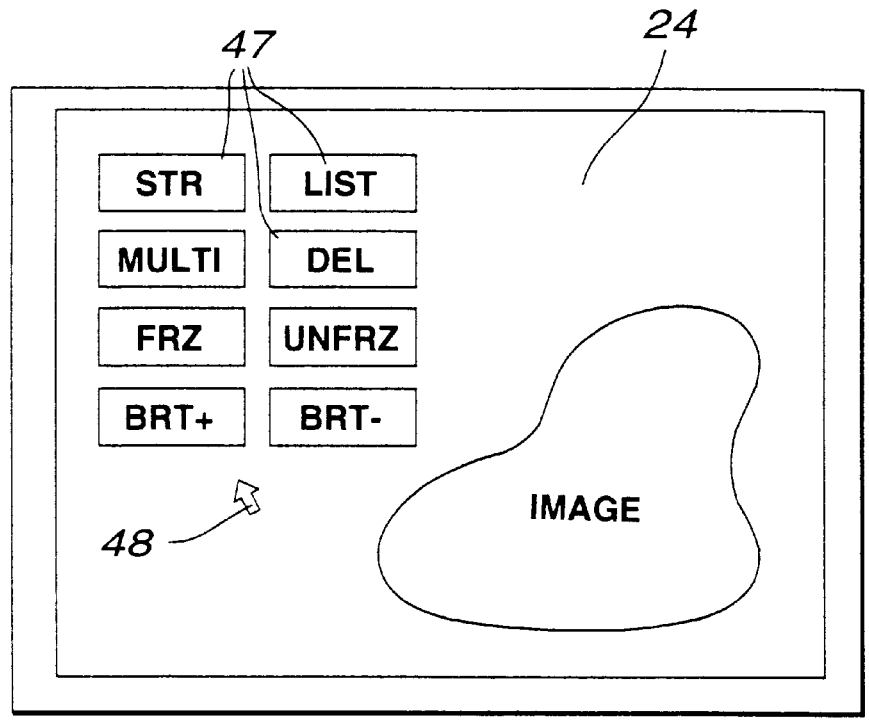

The image input/output circuit 42 has the ability to display graphic buttons 47 and cursor 48, which are shown in FIG. 7, on the monitor screen 24 under the control of the CPU 44.

The operation button set 25A on the operation unit 7 of the electronic endoscope 2, the operation button set 25B on the image processing apparatus 4, and the operation button unit 25C on the image collection and recording apparatus 41 are each composed of five push buttons and are analogous to one another in terms of the shapes and layout of the buttons. Each operation button set is composed of four direction buttons indicating up, down, left and right, and an E button for fulfilling the function of entering an instruction.

Operation information produced by handling the operation button set 25A on the electronic endoscope 2 and operation information produced by handling the operation button set 25B on the image processing apparatus 4 are transmitted to the CPU 44 in the image collection and recording apparatus 41. Operation information produced by handling the operation button set 25C included in the image collection and recording apparatus 41 itself and operation information produced by handling the mouse 45 are also input to the CPU 44.

The CPU 44 operates according to software stored in the hard disk 43, and comprehensively processes operation information input from each of the respective operating means.

FIG. 7 shows the monitor screen 24 in a normal use state. The plurality of graphic buttons 47 are displayed together with an image on the monitor screen 24. In this state, assume that the cursor 48 is moved to an STR graphic button 47, and the E button or the mouse button 46 is pressed in order to select a function associated with the selected graphic button. The CPU 44 in the image collection and recording apparatus 41 controls the image input/output circuit 42 so that a video signal currently input to the image input/output circuit 42, that is, an image being produced by the electronic endoscope 2, will be stored as image data in the hard disk 43.

When a LIST graphic button 47 is selected, the CPU 44 generates a list of image data items stored in the hard disk 43 to be displayed as shown in FIG. 8.

Figure 9:
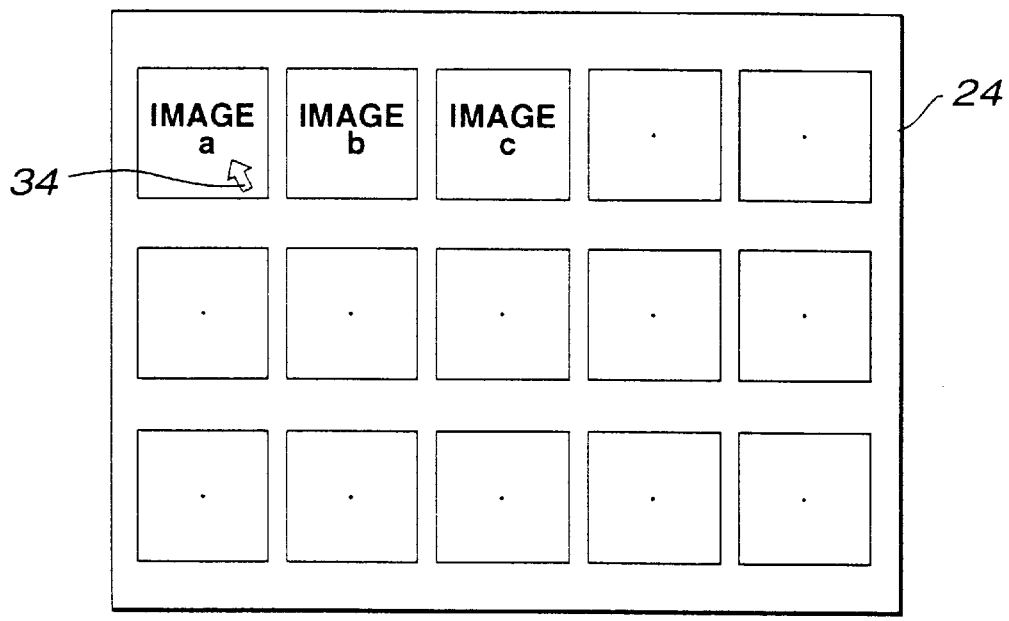

When a MULTI graphic button 47 is selected, image data items stored in the hard disk 43 are reduced in size and displayed simultaneously as image a, image b, image c, etc., shown in FIG. 9 (multi-image display).

In this state, when the cursor 34 is positioned on any image (image a in FIG. 9) and the mouse button 35 is pressed, the image can be displayed while enlarged.

When the DEL graphic button 47 is selected, a procedure is executed which deletes unnecessary items out of the image data items currently stored in the hard disk 43.

The graphic buttons 47 are associated with functions to be executed by the image collection and recording apparatus 41, while the FRZ, UNFRZ, BRT+, and BRT− graphic buttons 47 are associated with the functions to be executed by the image processing apparatus 4 as described in conjunction with the first embodiment.

When any of the graphic buttons 47 is selected, the CPU 44 in the image collection and recording apparatus 41 sends operation information to the CPU 27 in the image processing apparatus 4. The CPU 27 in the image processing apparatus 4 receives the information and carries out a given operation.

For the sake of brevity, the connector 9, light source apparatus 3, and other elements as shown in FIG. 3 are omitted from FIG. 6. Moreover, the signal lines 21 and 26 are linked to CPU 27 (not shown in FIG. 6) and operation button set 25A respectively.

This embodiment has an advantage as described below.

Operation information produced by handling the operating member included in the endoscope and image processing apparatus, respectively, is transmitted temporarily to the image collection and recording apparatus, and processed comprehensively together with operation information produced by handling the operating member included in the image collection and recording apparatus. If operation information indicates a request for a function of the image processing apparatus, the request is transmitted from the image collection and recording apparatus to the image processing apparatus, and then processed. A user can therefore use any of the operating members to operate the endoscope system, and can select and execute any of the functions of the endoscope system on one screen without being concerned about the apparatus with which the selected function is associated.

(Fourth Embodiment)

Next, the fourth embodiment of the present invention will be described with reference to FIG. 10. In this embodiment, a touch panel is included as an operating member.

Figure 10:
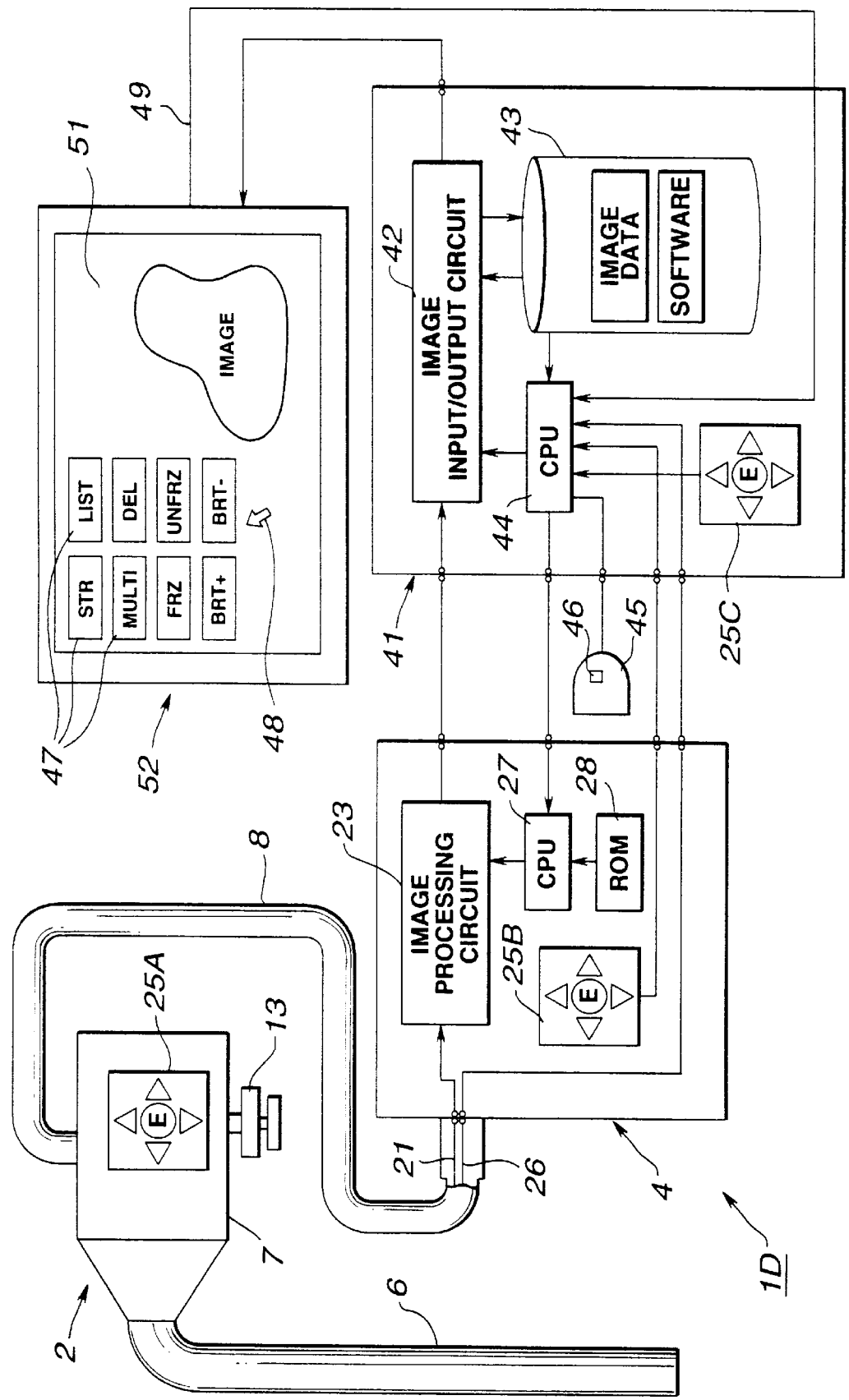
FIG. 10 is a block diagram showing the configuration of an endoscope system of the fourth embodiment of the present invention.

An endoscope system 1D of the fourth embodiment of the present invention shown in FIG. 10 has, in addition to the same components as those of the endoscope system 1C shown in FIG. 6, a touch panel-mounted LCD monitor 52 including a touch panel 51 in place of the monitor 5.

A video signal output from the image collection and recording apparatus 41 is supplied to an LCD monitor portion of the touch-panel mounted LCD monitor 52, whereby an image, graphic buttons 47, cursor 48, and the like are displayed.

The touch panel-mounted LCD monitor 52 has the touch panel 51 mounted on the monitor screen. The touch panel 51 serves as a transparent operation input means placed on the front surface of the LCD monitor screen. The coordinates of a position touched by a finger or pen are transmitted to the CPU 44 in the image collection and recording apparatus 41 over the signal line 49.

When a position in a specified graphic button 47 is touched with a finger or pen, the CPU 44 recognizes that the action is identical to the action of moving the cursor 48 to the position and of pressing the mouse button 46, and executes processing according to the selection.

This embodiment has an advantage as described below.

Handling of the respective operating members in the third embodiment as well as handling of the touch panel 51 are dealt with comprehensively. A user can select any one of the operating members and operate the endoscope system freely while viewing one kind of operation screen.

(Fifth Embodiment)

Figure 11:
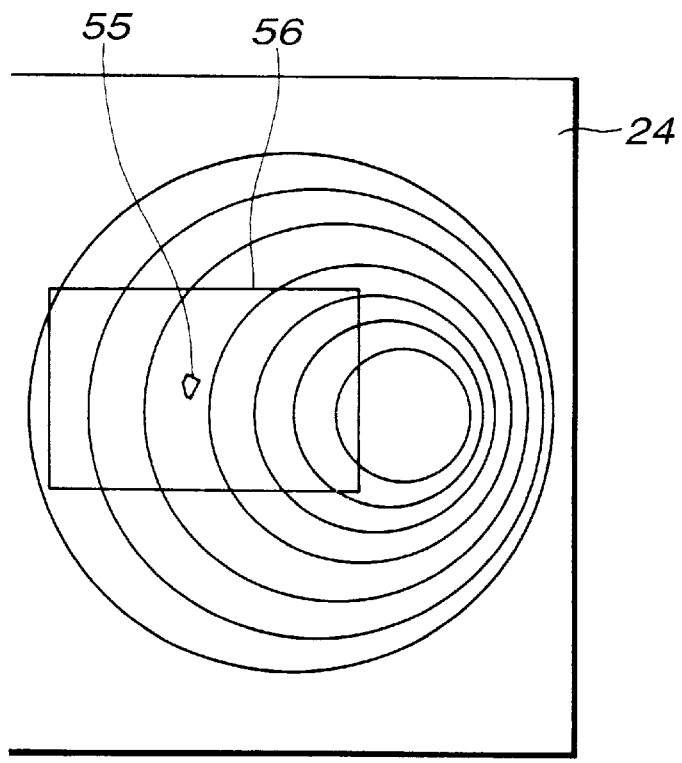
FIG. 11 is an explanatory diagram concerning the operation of an endoscope system of the fifth embodiment of the present invention.

Next, the fifth embodiment of the present invention will be described with reference to FIG. 11. FIG. 11 is an explanatory diagram showing the operation of the fifth embodiment of the present invention. In this embodiment, a specified area in an image can be designated using any operating members.

According to this embodiment, in an endoscope system 1D shown in FIG. 10, a user can use the graphic buttons to select a function of specifying part of a displayed image as an area.

A whole endoscopic image can be stored in the hard disk 43. However, to save the storage capacity of the hard disk 43 as much as possible, it is sometimes desirable to preserve only part of an image.

FIG. 11 shows the monitor screen 24 on which the interior of a pipe being inspected appears. As shown in FIG. 11, when there is a flaw 55 on the inner surface of the pipe, if it is desired to store a portion of an image containing the flaw 55, a graphic button for area specification that is not shown is selected in order to specify the portion containing the flaw 55 by defining an area specification frame 56. Thereafter, a storage function is executed.

In this way, only an area enclosed by the area specification frame 56 is stored in the hard disk 43. Compared with when a whole image is stored, the capacity of the hard disk 43 required for storage is drastically reduced. A large number of images can therefore be stored.

For moving the area specification frame, when the operation button set 25A, 25B, or 25C is used, any direction button is pressed. When the mouse 45 is used, the mouse 45 is moved and then the mouse button 46 is pressed. When the touch panel 51 is used, a finger or pen is put on any point on the displayed area specification frame 56, and dragged in a desired direction.

This embodiment has an advantage as described below.

When it is desired to store an area or desired portion of an image on the monitor screen 24, any operating member of the operation button 25A, 25B, or 25C, mouse 45, or touch panel 51 can be used to operate the endoscope system easily.

(Sixth Embodiment)

Figure 12:
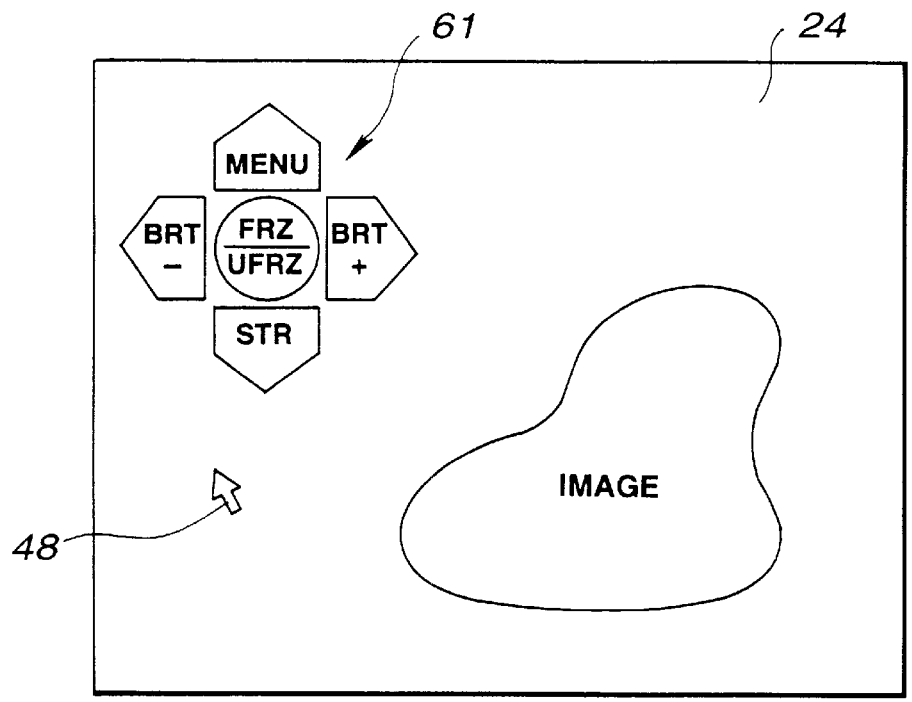
FIG. 12 is a diagram showing the monitor screen in the sixth embodiment of the present invention.

Next, the sixth embodiment of the present invention will be described with reference to FIG. 12. FIG. 12 shows a monitor screen in the sixth embodiment of the present invention. This embodiment provides a mode in which a specified function can be executed directly using an operation button set.

According to this embodiment, in the endoscope system 1D shown in FIG. 10, a user can use graphic buttons, which are not shown, to designate a button-specified direct function mode. In the second and third embodiments, pressing any direction button of an operation button set corresponds to, as mentioned previously, moving the cursor 34 or 48 using the mouse 33 or 45.

In this embodiment, an operation mode that is a button-specified direct mode is included. Once a user designates this mode, graphic buttons 61 shown in FIG. 12 appear on the monitor screen 24.

In this mode, the respective buttons of the operation button set 25A, 25B, or 25C shown in FIG. 10 do not work to move the cursor 48, but the five buttons are associated with the five graphic buttons appearing on the monitor screen 24 shown in FIG. 12.

When the E button of the operation button set is pressed, at wherever the cursor 48 is positioned, it is recognized as if the center graphic button 61 was pressed. An image is frozen, or if an image has already been frozen, the image is unfrozen.

When the Right direction button of the operation button set is pressed, it is recognized as if a BRT+ graphic button 61 is pressed. The brightness of an image is increased. When the Down direction button thereof is pressed, an image storage function is effectuated.

When the Up direction button of the operation button set is pressed, it is interpreted as if a MENU graphic button is pressed. When this button is pressed, the button-specified direct functioning mode is terminated, and the operation mode is returned to the normal mode described in the second or third embodiment. In the normal mode, when any direction button is pressed, the cursor 48 moves in the specified direction.

This embodiment has an advantage as described below.

In addition, to the normal mode in which the cursor 48 is moved by pressing any button of the operation button set 25A, 25B, or 25C, the button-specified direct function mode in which the buttons constituting the operation buttons set 25A, 25B, or 25C are associated directly with functions is included. Frequently-used functions can be executed easily in the button-specified direct functioning mode.

(Seventh Embodiment)

Next, the seventh embodiment of the present invention will be described with reference to FIGS. 13 and 14. This embodiment is such that an operation unit is provided with a microphone and voice data can be recorded in a recording means.

Figure 13:
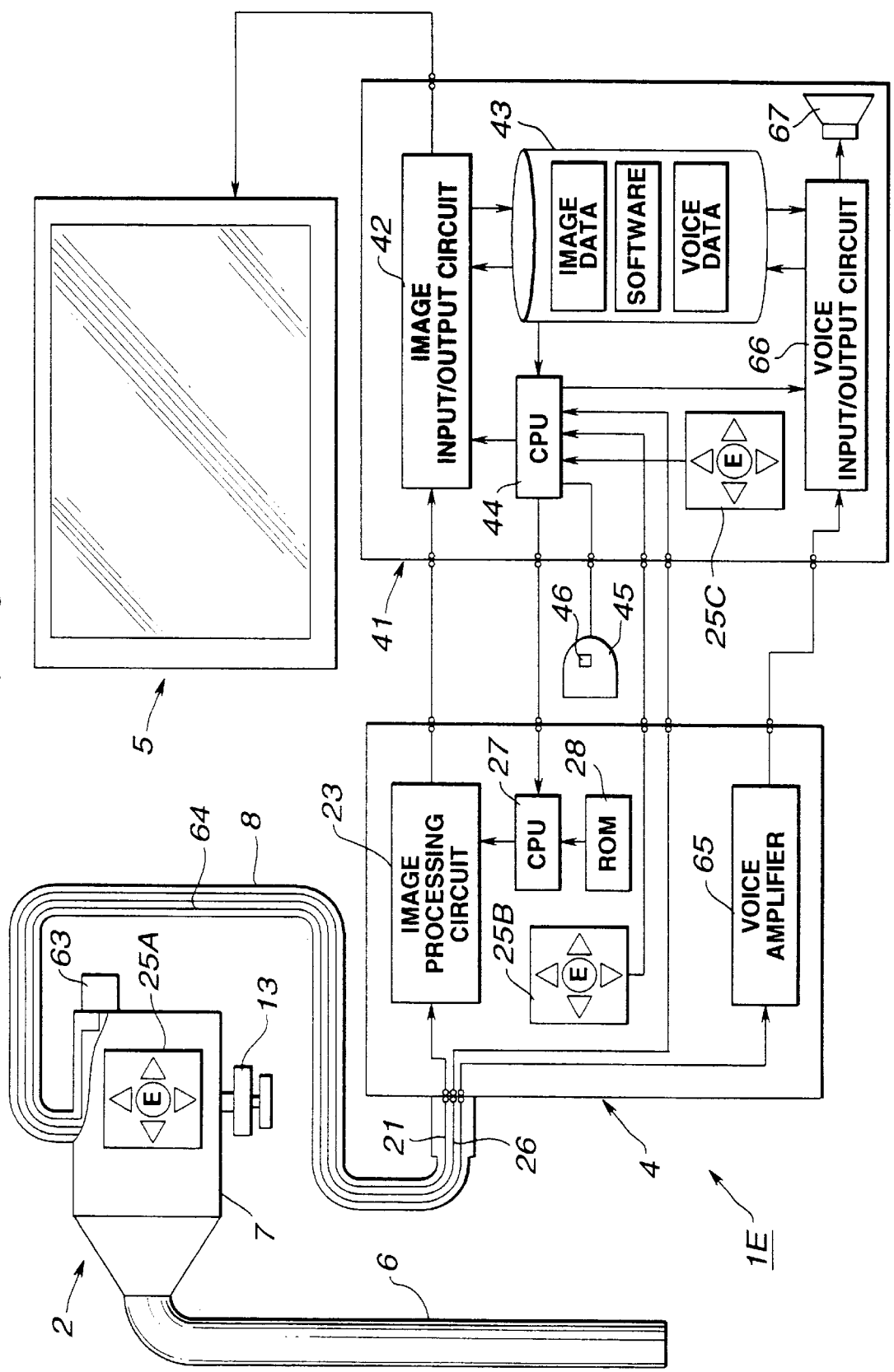

In an endoscope system 1E shown in FIG. 13 having the same components as those of the endoscope system 1C shown in FIG. 6, the operation unit 7 of the electronic endoscope 2 is provided with a microphone 63. A signal line 64 linked to the microphone 63 is routed to a voice signal amplifier 65 included in the image processing apparatus 4.

The voice signal amplifier 65 amplifies a signal sent from the microphone 63 and thus brings the signal level to the level at the line input thereof. The amplified voice signal is sent to the image collection and recording apparatus 41. The image collection and recording apparatus 41 includes a voice input/output circuit 66. A voice signal input to the image collection and recording apparatus 41 is, under the control of the CPU 44, output to a speaker 67 or converted into digital voice data and stored as voice data in the hard disk 43.

Moreover, under the control of the CPU 44, the voice input/output circuit 66 reads voice data stored in the hard disk 43 synchronously with reading of an image, and restores it to a voice signal so that the voice signal can be reproduced by the speaker 67.

Figure 14:
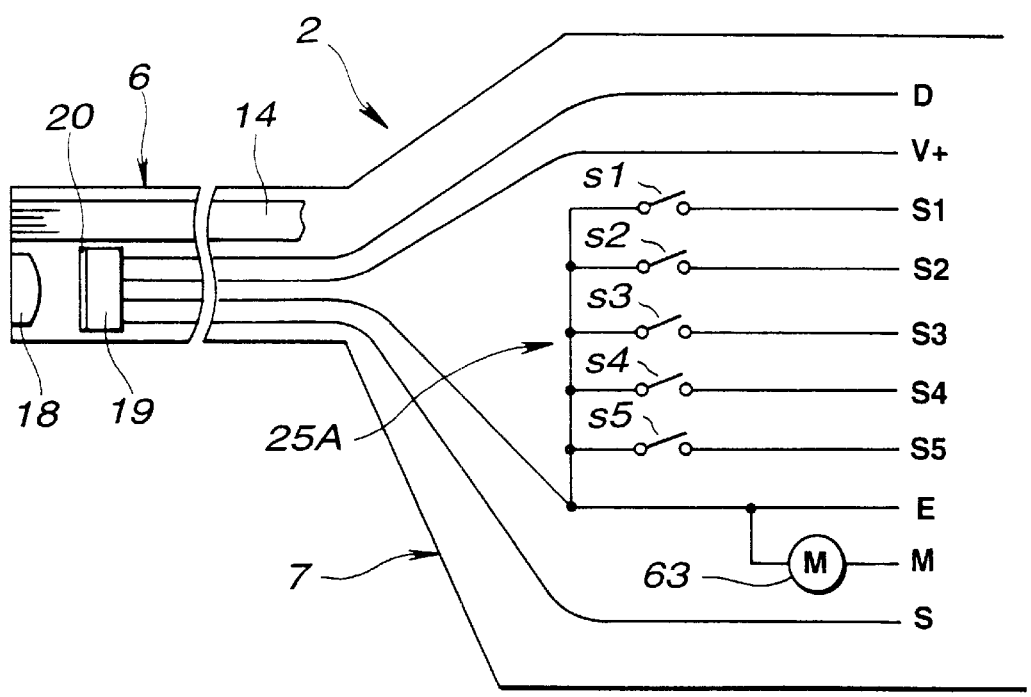
FIGS. 13 and 14 relate to the seventh embodiment of the present invention.

FIG. 14 shows an example of an internal wiring of the electronic endoscope 2 employed in the system shown in FIG. 13. Ten electrical wires shown on the right-hand side of FIG. 14 are extending from the electronic endoscope 2 and linked to the image processing apparatus 4.

A practical example of these ten electrical wires will be described below.

An electrical wire D is a line over which a driving signal used to drive the CCD 19 serving as an imaging device is supplied from the image processing apparatus 4 to the imaging device.

A electrical wire V+ is a line over which power is supplied from the image processing apparatus 4 to the imaging device.

Electrical wires S1 and S5 are lines linking contacts at one terminal of each of the five operation buttons s1 to s5 constituting the operation button set 25A and the image processing apparatus 4.

An electrical wire E is a grounding line linking in common a ground of the imaging device, a ground of the microphone 63, and contacts at the other terminals of the operation buttons s1 to s5.

An electrical wire M is a line over which a voice signal sent from the microphone 63 is transmitted.

An electrical wire S is a line over which an image signal taken by the imaging device is transmitted to the image processing apparatus 4.

In this embodiment, a voice picked up by the microphone 63 included in the operation unit 7 of the electronic endoscope 2 is amplified by the voice amplifier 65 in the image processing apparatus 4, and thus becomes a signal whose level is equivalent to the standard level at the line input of the amplifier.

The voice input/output circuit 66 in the image collection and recording apparatus 41 converts an input voice signal into voice data synchronously with storage of an image and stores the voice data in a digital form in the hard disk 43 under the control of the CPU 44. The voice input/output circuit 66 reads voice data synchronously with reading of an image, and restores it to a voice signal so that voice can be reproduced and output by the speaker 67.

This embodiment has an advantage as described below.

The operation unit 7 of the electronic endoscope 2 is provided with the microphone 63, and voice is converted into voice data synchronously with recording of an image and stored in the hard disk 43. While an image is read, voice recorded during recording of the image can be reproduced.

(Eighth Embodiment)

Next, the eighth embodiment of the present invention will be described with reference to FIGS. 15 and 16. This embodiment is such that an operation signal produced by handling any operation button on an endoscope is input to an encoder in the endoscope, and transmitted as an encoded signal over a smaller number of signal lines than the number of operation buttons.

Figures 15, 16:
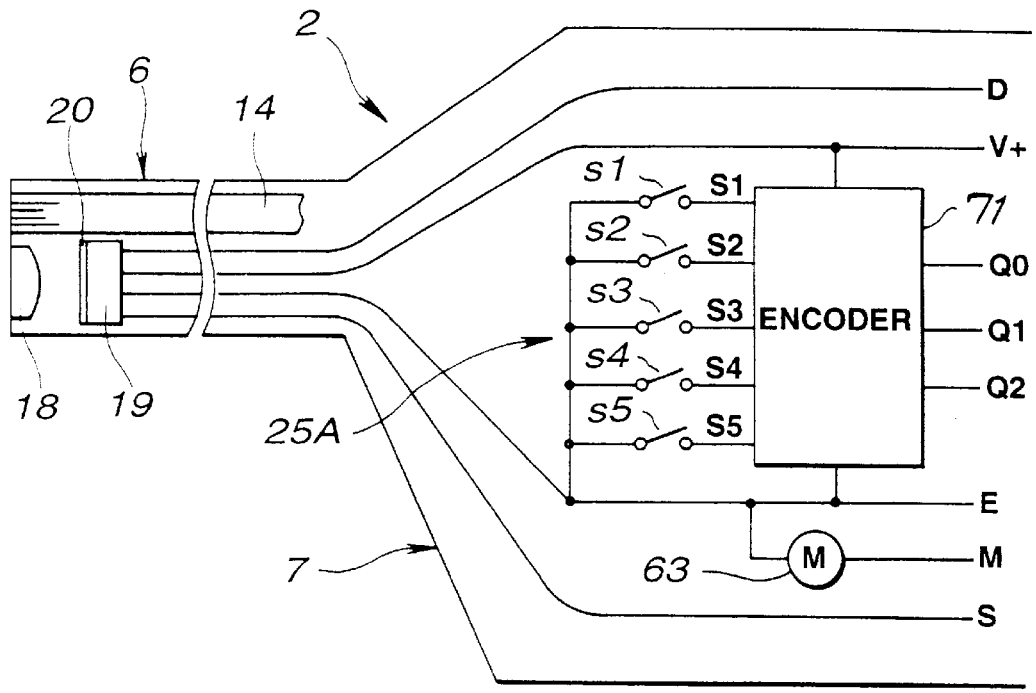
FIGS. 15 and 16 relate to the eighth embodiment of the present invention.

The endoscope system of this embodiment has the same components as the one shown in FIG. 13, but has, as shown in FIG. 15, an encoder 71 included in the operation unit 7 of the electronic endoscope 2.

The contacts at one terminal of each of the operation buttons s1 to s5 constituting the operation button set 25A are connected to an input terminal of the encoder 71. Outputs Q0, Q1, and Q2 of the encoder 71 are input to the image processing apparatus 4 over electrical wires Q0 to Q2 (For the sake of brevity, the outputs of the encoder 71 and the electrical wires over which the outputs are transmitted are denoted with the same reference numerals Q1 (i=0, 1, or 2). Moreover, outputs of the operation buttons s1 to s5 are denoted with S1 to S5.).

The number of lines linking the electronic endoscope 2 and image processing apparatus 4 is eight, which is two fewer than the number of lines shown in FIG. 14. The encoder 71 encodes the outputs S1 to S5 of the operation buttons s1 to s5 according to the list shown in FIG. 16, and outputs results over the three signal lines Q0, Q1, and Q2.

Even when seven operation buttons s1 to s7 are included to provide outputs to S7, the number of signal lines may still be three. That is to say, operation information produced by handling any operation button can be transmitted using fewer signal lines than the number of operation buttons.

To the encoder 71, power must be supplied and a ground must be connected. These are fundamentally required by the electronic endoscope 2 and have therefore already been achieved. For constructing the encoder 71 employed in this embodiment, a semiconductor MC14532B (8-bit priority encoder) manufactured by Motorola Inc. may be utilized.

This embodiment has an advantage as described below.

The number of connection lines linking the electronic endoscope 2 and image processing apparatus 4 should be as small as possible for the purpose of reducing the costs of line materials and connectors. According to this embodiment, operation information can be transmitted using fewer signal lines than the number of switches in an operating member. Consequently, the costs can be reduced.

(Ninth Embodiment)

The ninth embodiment of the present invention will be described with reference to FIG. 17. This embodiment provides an RS232C interface to enable communication between an image processing apparatus and image collection and recording apparatus such that surplus electrical wires linked to the RS232C interface may be used to transmit another signals.

Figure 17:
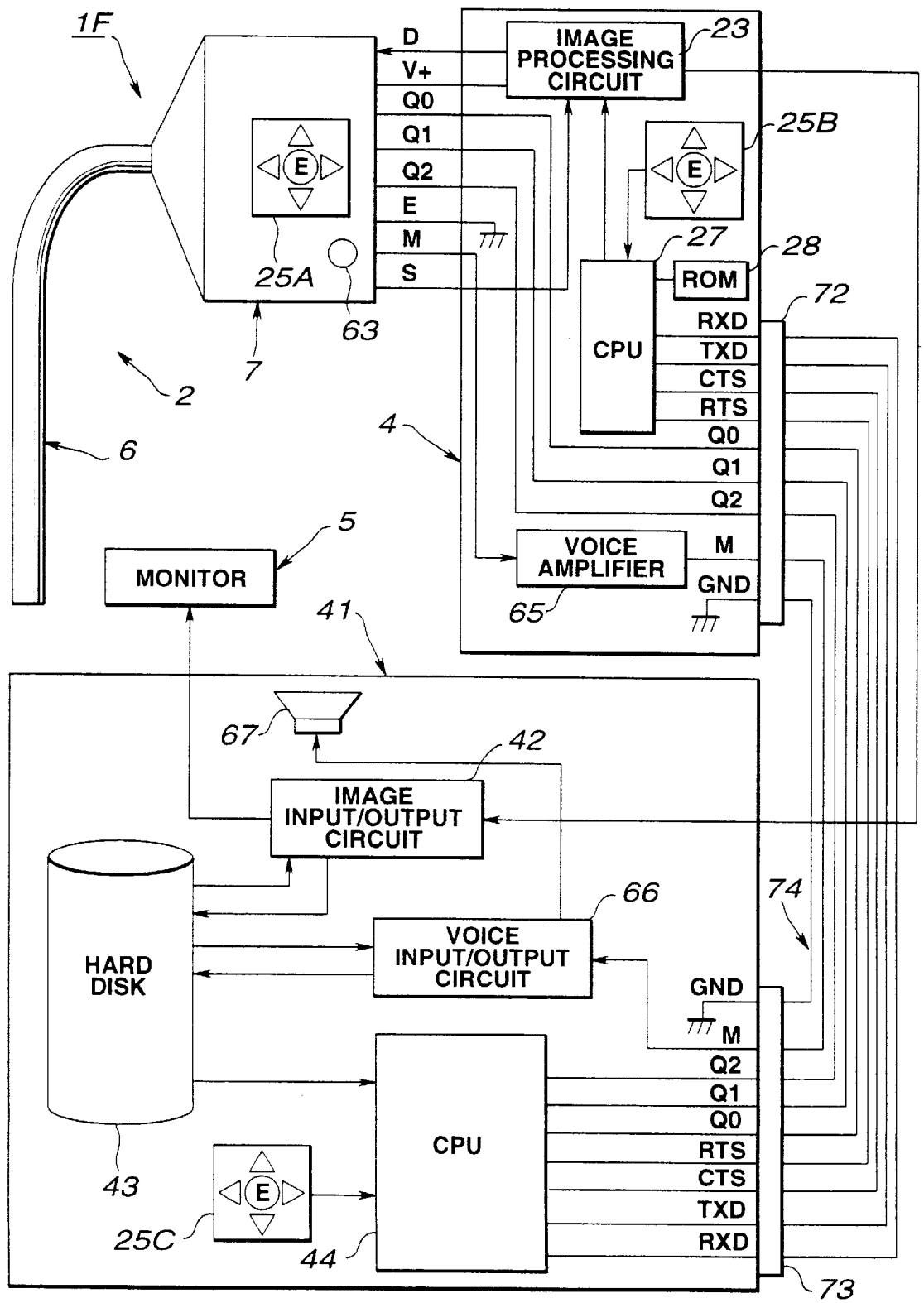
FIGS. 17 and 18 relate to the ninth embodiment of the present invention.

FIG. 17 shows in detail actual linkage of electrical wires among the electronic endoscope 2, image processing apparatus 4, and image collection and recording apparatus 41 in an endoscope system 1F of this embodiment. The image processing apparatus 4 and image collection and recording apparatus 41 are linked by an RS232C cable 74 spliced with RS232C connectors 72 and 73 at both ends thereof.

Moreover, the electronic endoscope 2 adopts the same wiring as the one shown in FIG. 15.

Specifically, an electrical wire D is a line over which a driving signal used to drive an imaging device is transmitted from the image processing apparatus to the imaging device.

An electrical wire V+ is a line through which power is supplied from the image processing apparatus to the imaging device.

Electrical wires Q0, Q1, and Q2 are lines over which operation information produced by handling the operation button set 25A is transmitted after being encoded.

An electrical wire E is a grounding line used in common among different elements in the electronic endoscope system as discussed above.

An electrical wire M is a line over which a voice signal sent from the microphone is transmitted.

An electrical wire S is a line over which an image signal taken by the imaging device is transmitted to the image processing apparatus.

An image signal taken by the electronic endoscope 2 is input to the image processing apparatus 4 over the electrical wire S, and processed by the image processing circuit 23. This results in a standard video signal. The video signal is sent to the image collection and recording apparatus 41.

Figure 18:
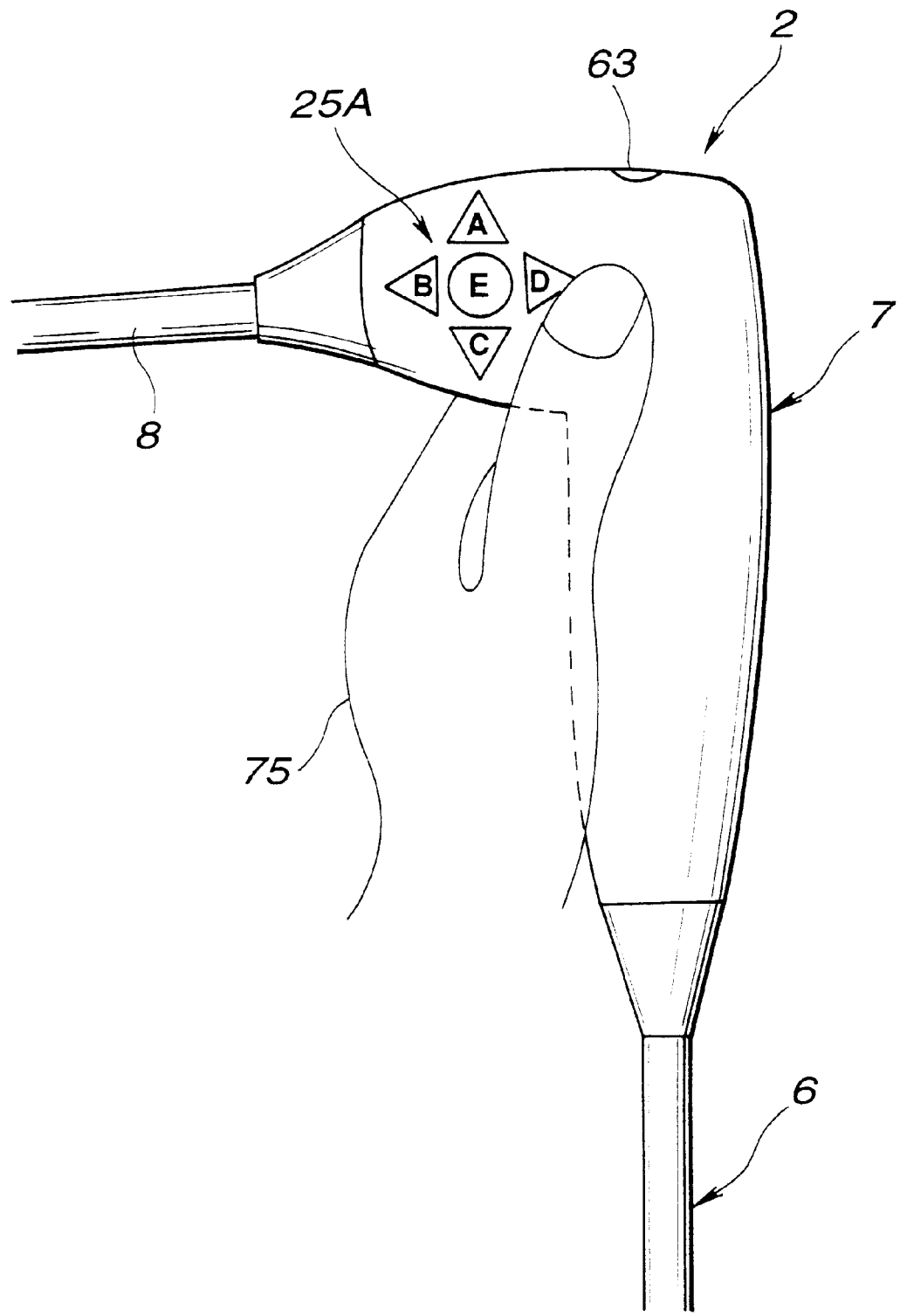

The operation unit 7 of the electronic endoscope 2 is, as shown in FIG. 18, provided with the operation button set 25A.

The operation unit 7 of the electronic endoscope 2 is usually held by one hand 75. This is because the other hand is often engaged in handling the insertion unit 6 of the electronic endoscope 2. The operation button set 25A located on the operation unit 7 can preferably be handled by only one hand 75 by which the operation unit 7 is held. The operation unit 7 is therefore designed as shown in FIG. 18 so that any button of the operation button set 25A can be pressed by the thumb.

Operation information produced by handling the operation button set 25B located on the image processing apparatus 4 is, according to this embodiment, input temporarily to the CPU 27 in the image processing apparatus 4, and then transmitted to the CPU 44 in the image collection and recording apparatus 41.

The CPU 27 in the image processing apparatus 4 and the CPU 44 in the image collection and recording apparatus 41 communicate with each other to transfer various kinds of information necessary for the apparatuses to be interlocked with each other including the operation information. In recent years, a widely prevailing method of communication to be performed between the apparatuses is communication based on an RS232C interface. The RS232C is an interface standard stipulating a method of connecting a modem to a computer for transmitting data over a telephone line. According to the interface standard RS232C, a 9-pin connector spliced with nine electrical wires is generally employed.

In addition to the above objective, the RS232C interface has been widely adopted for the communication of data directly between the apparatuses without a modem. In this case, not all of the nine electrical wires are needed. only five electrical wires including electrical wires used to transmit an RXD signal (terminal reception data), TXD signal (terminal transmission data), CTS signal (Transmission Enabled), and RTS signal (transmission request), and a grounding (GND) wire are needed.

However, since the RS232C cable including nine conductors and having 9-pin connectors for RS232C interface has widely prevailed, when such cable is used, the lowest cost can be realized. Furthermore, the RS232C cable is readily available as a component for construction purposes. In this embodiment, therefore, the RS232C cable 74 is employed. Four additional electrical wires are used to transmit encoded operation information produced by handling the operation button set 25A along with a voice signal.

This embodiment has an advantage as described below.

Since an RS232C interface is adopted for communication between the image processing apparatus 4 and image collection and recording apparatus 41, surplus electrical wires that are not required for the operation of the electronic endoscope 2 can be used to transmit operation information produced by handling an operating means of an amplified voice signal. The number of cables required to link the image processing apparatus 4 and image collection and recording apparatus 41 becomes very small. This results in easy connections.

(Tenth Embodiment)

Next, the tenth embodiment of the present invention will be described with reference to FIGS. 19A and 19B. An operating member included in the electronic endoscope 2 is composed of five push buttons. Two sets of operating members are located on the left and right side surfaces of the operation unit 7.

The hand 75 handling operation unit 7 of the electronic endoscope in the ninth embodiment is, as shown in FIG. 18, the left hand. In this case, the right hand is presumably used to handle the insertion unit 6 of the electronic endoscope 2. However, the leading hand depends on the person using the apparatus. Some persons may handle the operation unit 7 with his/her right hand and the insertion unit 6 with his/her left hand.

Figure 19A:
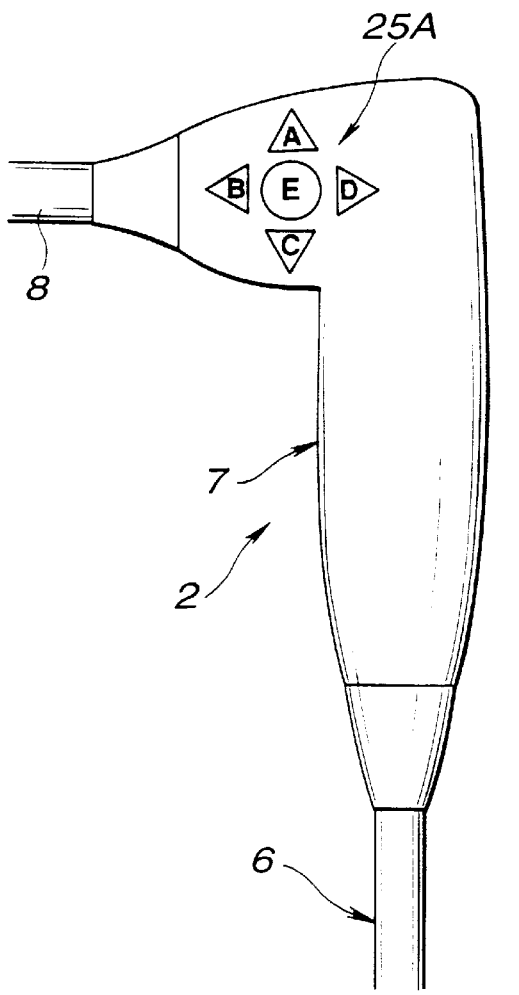
FIGS. 19A and 19B are the left and right side views of the operation unit of the electronic endoscope in the tenth embodiment of the present invention.
Figure 19B:
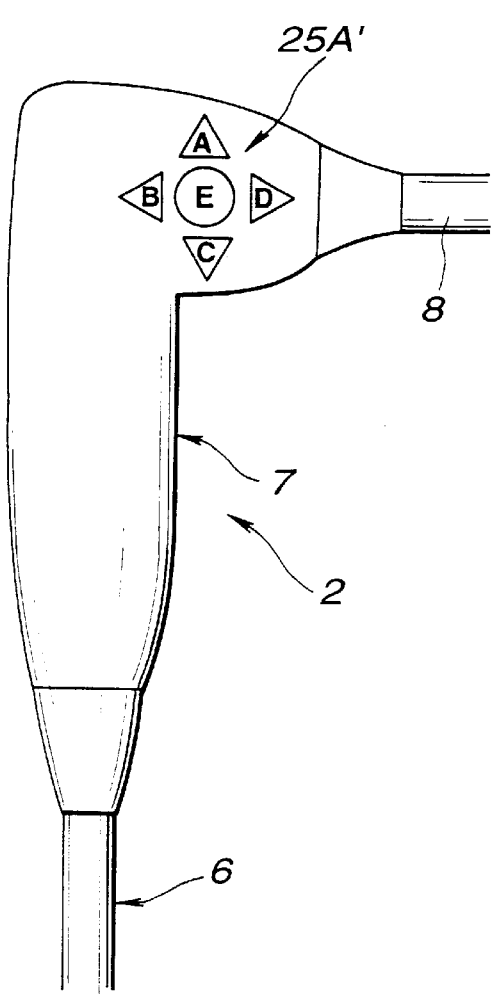

When the operation button sets 25A and 25A' are, as shown in FIGS. 19A and 19B, located on the left and right side surfaces of the operation unit 7, the operation unit can be used readily by any person using either the right hand or the left hand as the leading hand. The wirings of the operation button sets 25A and 25A' should be routed to the encoder 71 shown in FIG. 15 with electrical wires extending from the two sets of five buttons gathered together.

This embodiment has an advantage as described below.

Since the operation button sets 25A and 25A' are located on the left and right side surfaces of the operation unit 7, the operation unit can be used readily by any person using either the right hand or left hand as the leading hand.

The aforesaid embodiments have been described with the assumption that the functions provided by the image processing apparatus 4 for driving the imaging device incorporated in the electronic endoscope 2 and for processing an output signal of the imaging device, and the functions provided by the image collection and recording apparatus 41 can be controlled mainly.

Alternatively, the present invention can apply to a mode in which functions provided by the endoscope are controlled as described in conjunction with the next embodiment.

(Eleventh Embodiment)

Next, the eleventh embodiment of the present invention will be described with reference to FIGS. 20 and 21. In this embodiment, an optical system whose image magnification power can be varied is included in the electronic endoscope 2. A function for varying the power is controlled as described below.

Figure 20:
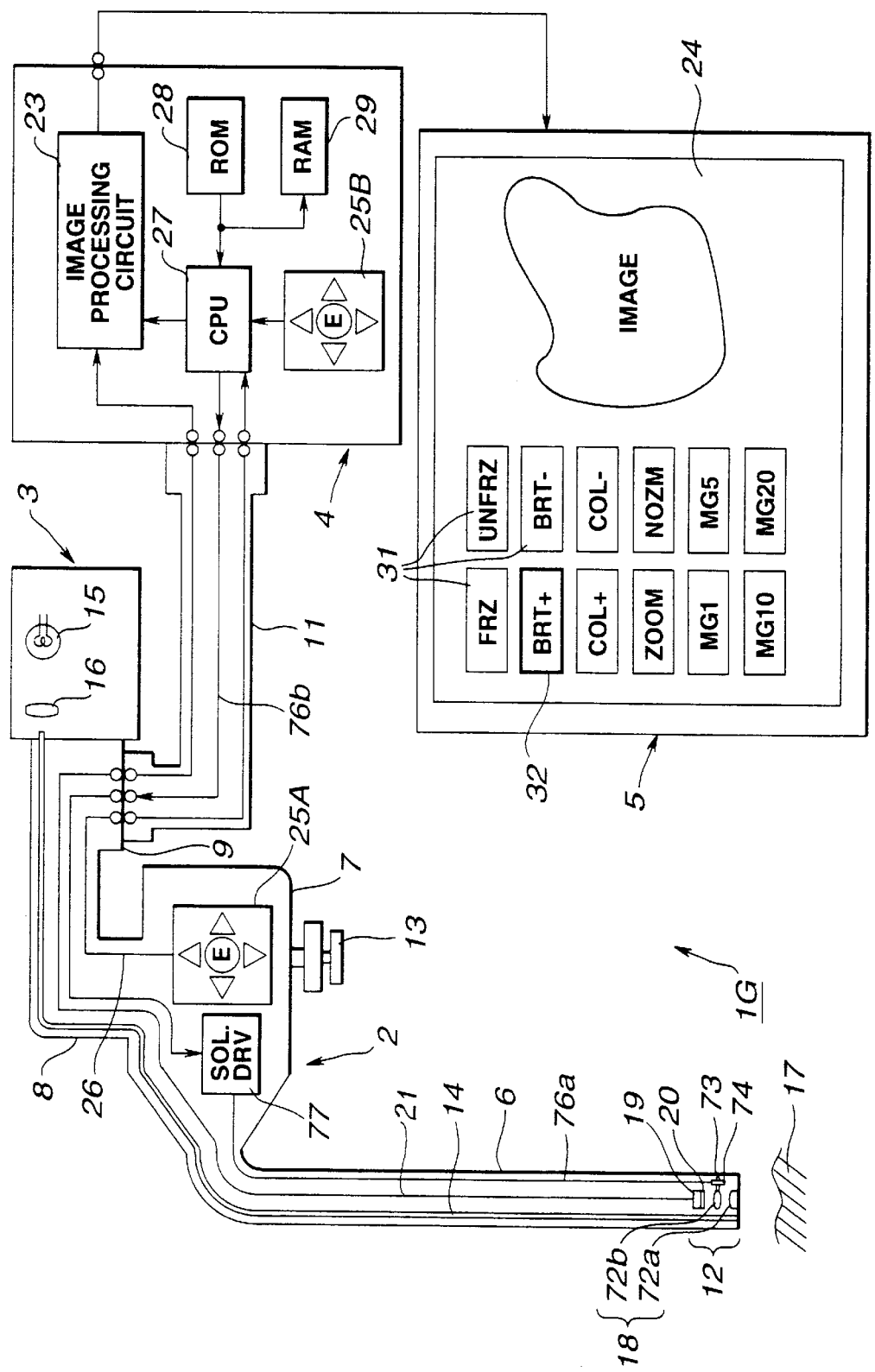

An electronic endoscope system 1G shown in FIG. 20 includes the same components as the endoscope system 1A shown in FIG. 1, and further provides a power variation function in the objective lens assembly 18.

Figure 21:
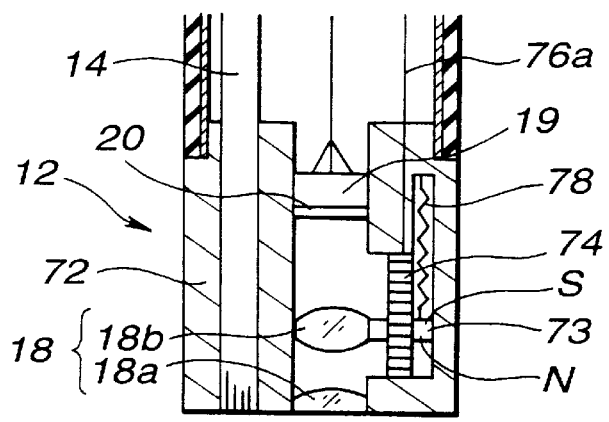
FIGS. 20 and 21 relate to the eleventh embodiment.

As shown in FIG. 21, a main distal-part unit 72 forming the distal part 12 has a second lens 18b, which functions as a power variation lens located on the optical axis of a first lens 18a forming the objective lens 18. A movable magnet 73 attached to the second lens 18b is freely movable in the optical-axis direction by means of a solenoid (cylindrical coil) 74 placed in the main distal-part unit 72.

For example, the (coil of) solenoid 74 is placed parallel to the optical axis of the objective lens 18, and penetrated through a hole of the movable magnet 73. Both ends of the solenoid 74 are fixed to the main distal-part unit 72. The movable magnet 73 is freely movable within a moving range defined by the length of the solenoid 74 in the longitudinal direction.

The solenoid 74 has, for example, a tap in the center thereof. The solenoid 74 is connected to a solenoid driver 77, which applies a driving signal to the solenoid and is incorporated in the operation unit 7, by way of a signal line 76a, and is also connected to the CPU 27 in the image processing apparatus 4 by way of a signal line 76b.

The movable magnet 73 is constrained by means of a spring 78 having a weak elasticity. When the solenoid driver 77 is not actuated, the movable magnet 73 is located at the proximal back end because of the elasticity of the spring 78. In this state, the power variation function is least effective, and the magnification power of the objective lens is 1.

Moreover, the solenoid driver 77 is actuated in order to output a driving signal to move the solenoid toward the distal end in the longitudinal direction, with respect to the solenoid 74. This causes the movable magnet 73 to move in a direction parallel to the optical axis against the elasticity of the spring 78. According to the level of the driving signal, the solenoid can be set to a position at which the magnification power of the objective lens 18 becomes 5 times, 10 times, or 20 times.

Moreover, in this embodiment, a function mark indicating that the magnification power of the objective lens is set to, for example, 1 times, 5 times, 10 times, or 20 times is displayed on the display plane 24 of the monitor 5 to assist in operating the magnification power variation function.

A user handles, as described in conjunction with the first embodiment, the operation button set 25A or 25B, so as to move the cursor 32 to, for example, an MG5 function mark, and presses the E button. Thus, an instruction signal instructing the magnification power to be varied to 5 times is sent to the CPU 27.

The CPU 27 in turn sends a control signal used to vary the magnification power to 5 times to the solenoid driver 77 over the signal line 76b. The solenoid driver 77 sends a driving signal, which causes the back end of the solenoid to work as the south pole, to a coil portion between the back end of the solenoid and the center tap. The movable magnet 73 is then driven to the intermediate position between the back end of the solenoid 77 and the center tap. Consequently, the objective lens 18 is set to an image formation state in which an image that is five times larger than an object image is formed.

The objective lens can be set to any state in which any other power is attained.

According to this embodiment, enlargement can be achieved through image processing. If image quality deteriorates, the image formation state of the objective lens 18 itself may be varied. Thus, enlargement and observation can be achieved with good image quality. The other advantages are the same as those provided by the first embodiment.

In the aforesaid embodiments, the electronic endoscope 2 in which the imaging device is incorporated in the distal part of the insertion unit 6 is adopted as an endoscope. Aside from the endoscope 2, the present invention can be adapted to an optical endoscope having an image guide used to transmit an optical image or a TV camera externally-mounted endoscope having a TV camera in which an imaging device is incorporated in an eyepiece unit of the optical endoscope mounted thereon.

In the eleventh embodiment, a function relevant to the objective optical system or imaging device included in the electronic endoscope 2 is executed by handling the operation button set. The present invention can also apply to instruction of a function unrelated to the objective optical system or imaging device.

For example, a bending driving mechanism for driving and bending the bending part of an endoscope or one of the components constituting an endoscope may be formed with an electrical bending driving mechanism such as a motor. A bending button serving as a bending instructing means is located at a plurality of positions, such as the operation unit of the electronic endoscope 2 and a bending driving unit in which the electrical bending buttons is used in the same way to instruct bending, so that bending can be achieved in a direction corresponding to the bending instruction.

In this case, the present invention can be adapted not only to an endoscope system including an endoscope in which an imaging device is incorporated but also to an endoscope system including an optical endoscope.

Incidentally, even an embodiment constructed by combining the aforesaid embodiments partly belongs to the present invention.

What is claimed is:

1. An endoscope system, comprising:

an endoscope including an elongated insertion unit, an emitting means for emitting illumination light through the distal part of said insertion unit, an objective lens assembly located in said distal part for forming an image of an object illuminated by the illumination light, and an imaging device for photoelectrically converting the image;

an image processing apparatus for processing an image signal output from said imaging device and producing a standard video signal from said image signal;

a monitor for displaying the standard video signal;

a first operating member connected to said endoscope and having a first operation switch set;

a second operating member connected to said image processing apparatus and having a second operation switch set, wherein said first and second operation switch sets have the same structure;

a control means, connected to said first and second operating members, for controlling at least one function provided by said endoscope system in response to operation of either of the first and second operating members, said control means controlling said at least one function in the same manner regardless of which one of said first and second operating members is operated;

a function display means for displaying on said monitor function marks associated with functions provided by said endoscope system; and a cursor mark used to select any of the function marks on said monitor.

2. An endoscope system according to claim 1, wherein said control means includes a central processing unit.

3. An endoscope system according to claim 1, wherein said at least one function provided by said endoscope system includes an image processing function installed in said image processing apparatus.

4. An endoscope system according to claim 1, wherein said at least one function provided by said endoscope system is installed in said image processing apparatus and includes a display function of displaying an image on said monitor.

5. An endoscope system according to claim 4, wherein said display function includes at least one of a still image display function of displaying a still image, a luminance change function of changing the brightness level of an image displayed on said monitor, a color change function of changing the color tone of an image displayed on said monitor, and a zoom function for enlarging an image displayed on said monitor.

6. An endoscope system according to claim 1, wherein said at least one function provided by said endoscope system includes a function installed in said endoscope.

7. An endoscope system according to claim 1, wherein said first and second operating members each include a plurality of movement key-switches used to instruct movements in a plurality of directions; and a decision key-switch used to instruct a decision.

8. An endoscope system according to claim 1, wherein said first and second operating members each include a plurality of movement key-switches used to instruct movements in a plurality of directions; and an execution key-switch used to instruct execution, wherein said movement key-switches are used to move said cursor mark to any of said function marks, and said execution key-switch instructs said control means to execute the function associated with the function mark designated by said cursor mark.

9. An endoscope system according to claim 1, further comprising an image collection and recording apparatus capable of recording and reproducing image data produced by said image processing apparatus.

10. An endoscope system according to claim 9, wherein said image collection and recording apparatus includes a third operating member having a third operation switch set whose structure is the same as that of the first and second operation switch sets of said first and second operating members, respectively.

11. An endoscope system according to claim 9, further comprising an RS232C connector used for communication between said image processing apparatus and said image collection and recording apparatus, wherein said RS232C connector provides connection for image signal data transmission between said image processing apparatus and said image collection and recording apparatus and for additional signal lines used to transmit other signals.

12. An endoscope system according to claim 1, further comprising a voice collection and recording apparatus for recording and reproducing voice information.

13. An endoscope system according to claim 1, wherein said first operating member included in said endoscope has an encoder for encoding a signal passed by said first operation switch set.

14. An endoscope system according to claim 1, wherein said endoscope further includes a hand-held unit at a proximal end of said insertion unit, wherein said first operating member is located at a position on said hand-held unit at which said first operating member can be handled easily with said hand-held unit being held by a user's left hand, and said system further comprises a third operating member having a third operation switch set having a structure which is the same as that of the first operation switch set of said first operating member, wherein said third operating member is located at a position on said hand-held unit at which said third operating member can be handled easily with said hand-held unit being held by a user's right hand.

15. An endoscope system, comprising:
an endoscope having an imaging device for imaging an object;
an image processing apparatus for processing an image produced by said imaging device;
a display device for displaying the processed image;
a first operating member and a second operating member, said first and second operating members being designed to function in the same way and are located on said endoscope and on said image processing apparatus, respectively, to execute image processing functions installed in said image processing apparatus;
a controller, electrically coupled to said first and second operating members, for controlling an image processing function selected by handling either of said first or second operating members;
a function display means for displaying on said display means a plurality of function marks associated with the image processing functions; and
a cursor mark used to select any one of the plurality of function marks on said monitor.

16. An endoscope system, comprising:
an endoscope having an imaging device for imaging an object;
an image processing apparatus for processing an image produced by said imaging device;
a display device for displaying the processed image;
a first operating member and a second operating member, wherein said first and second operating members are both capable of selecting and executing each one of a plurality of functions associated with said endoscope system, including at least one image processing function; and
a controller, electrically coupled to said first and second operating members, for controlling a function selected with either of said first or second operating members, wherein the display device is adapted to also display a representation for each of said plurality of functions and a selection indicator to indicate the function being selected.

17. An endoscope system according to claim 16, wherein at least one of said first and second operating members comprises
a plurality of direction buttons to move said selection indicator to each function representation on said display device; and
a selection entry button to execute a selected function by sending the selection to said controller.

18. An endoscope system according to claim 17, wherein one of said plurality of functions is an operating mode of said first and second operating members such that each direction button and said entry selection button is directly associated with one of said plurality of functions, whereby when one of said buttons is pressed, the function associated with that button is directly selected to the controller.

19. An endoscope system according to claim 17, further comprising an encoder such that the number of connections required between said controller and said at least one operating member is fewer than the number of buttons in said at least one operating member.

20. An endoscope system according to claim 16, wherein at least one of said first and second operating members comprises a computer mouse for moving said selection indicator to a desired function, said computer mouse including a selection entry button to execute a selected function by sending the selection to said controller.

21. An endoscope system according to claim 16, wherein one of said first and second operating members is disposed on said display device as a touch sensitive panel, such that a function associated with a displayed function representation is selected when touched by a user.

22. An endoscope system according to claim 16, further comprising an image collection and recording apparatus for recording or reproducing image data to or from a data storage unit, said image collection and recording apparatus being electrically connected to said image processing apparatus and said display device.

23. An endoscope system according to claim 22, wherein said image collection and recording apparatus is capable of retrieving and displaying image data for a plurality of recorded images on said display device.

24. An endoscope system according to claim 22, wherein said image collection and recording apparatus is capable of recording only a portion of a displayed image indicated by a selection window on said display device, and wherein a location of the selection window is controlled by either of said first or second operation members.

25. An endoscope system according to claim 22, further comprising a voice collection and recording mechanism for recording or reproducing a voice signal.

26. An endoscope system according to claim 16, wherein said plurality of functions associated with said endoscope system includes at least one of the following features: zoom/unzoom, brightness increase/brightness decrease, color tone enhancement/color tone lightening, image freeze/unfreeze, image storage, image retrieval, image deletion, image magnification, voice storage, and voice retrieval.

* * * * *